US006203988B1

(12) United States Patent
Kambara et al.

(10) Patent No.: US 6,203,988 B1
(45) Date of Patent: Mar. 20, 2001

(54) DNA FRAGMENT PREPARATION METHOD FOR GENE EXPRESSION PROFILING

(75) Inventors: Hideki Kambara, Hachioji; Chihiro Uematsu, Kawasaki, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/228,942

(22) Filed: Jan. 12, 1999

(30) Foreign Application Priority Data

Jan. 14, 1998 (JP) .................................................. 10-005399

(51) Int. Cl.[7] .............................. C12Q 1/68; C12P 19/34; C07H 21/04; C07H 21/00
(52) U.S. Cl. .................... 435/6; 435/91.2; 435/91.52; 536/24.3; 536/25.32
(58) Field of Search ........................... 435/6, 91.2, 91.52; 536/24.3, 25.32

(56) References Cited

U.S. PATENT DOCUMENTS 5,314,809 * 5/1994 Erlich et al. ......................... 435/91.2

FOREIGN PATENT DOCUMENTS

| 6-174693 | 6/1994 | (JP) | .............................. G01N/27/447 |
| 7-181164 | 7/1995 | (JP) | .............................. G01N/27/447 |

OTHER PUBLICATIONS

Chehab et al. Detection of specific DNA sequences by fluorescence amplification: a color complementation assay, Proc. Natl. Acad. Sci. USA, vol. 86, pp. 9178–9182, 1989.*

Nature Biotechnology, vol. 14, Dec. 1996, "Expression monitoring by hybridization to high–density oligonucleotide arrays", D. Lockhart et al, pp. 1675–1680.

Proc. Natl. Acad. Sci. USA, vol. 93, Oct. 1996, "Parallel human genome analysis: Microarray–based expression monitoring of 1000 genes", M. Schena et al, pp. 10614–10619.

FEBS Letters,351, 1994, "Fluorescent differential display: arbitrarily primed RT–PCR fingerprinting on an automated DNA sequencer", T. Ito et al, pp. 231–236.

Nucleic Acids Research, 1996, vol. 24, No. 13, "AFLP–based nRNA fingerprinting", T. Money et al, pp. 2616–2617.

Nucleic Acids Symposium, Series No. 35, 1996, "Measurement of mRNA expression by selective amplification of cDNA restriction fragments with selective primers", C. Uematsu et al, pp. 257–258.

* cited by examiner

Primary Examiner—W. Gary Jones
Assistant Examiner—Joyce Tung
(74) Attorney, Agent, or Firm—Mattingly, Stanger & Malur, P.C.

(57) ABSTRACT

A DNA fragment preparation method for DNA analysis comprising, i) preparing a plurality of DNA fragments from a sample DNA, and ii) amplifying a specific DNA fragment by PCR, using a pair of primers which hybridize with terminus sequences of the DNA fragments, and a specific primer which hybridizes specifically with a base sequence of the specific DNA fragment at a position between a priming site of one of primer the pair of primers and a priming site of another primer of the pair of primers. The specific primer hybridizes specifically with a base sequence at a middle position of the specific DNA fragment. Products of PCR are separated, by electrophoresis, and signals from DNA fragments originated in a known genes and signals from DNA fragments originated in a unknown genes are displayed separately on a display.

15 Claims, 7 Drawing Sheets

SEQUENCE LISTING

<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 1
gttttcccag tcacgac                                                  17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 2
caggaaacag ctatgac                                                  17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 3
attaaccctc actaaag                                                  17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 4
aatacgactc actatag                                                  17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 5
cgaggtcgac ggtatcg                                                  17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 6

-continued

```
tctagaacta gtggatc                                              17

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 7
tctccaaaaa aaaaaaaaaa                                           20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ligated to 3' end of DNA fragment

<400> SEQUENCE: 8
tgtggttttt tttttttttt t                                         21
```

DNA FRAGMENT PREPARATION METHOD FOR GENE EXPRESSION PROFILING

BACKGROUND OF THE INVENTION

1. Field of the Invention

This invention relates to a DNA fragment analysis method including comparative DNA analysis as well as gene expression profiling.

2. Description of the Related Art

With the progress of the human genome project, the whole genome structure and the genomic DNA base sequences have been being clarified. The next step is to analyze gene functions coded in genomes. Comparative analysis of genomes or DNA fragments as well as gene expression profiling play an important role in the function analysis.

All the inherited information is written in genome. The information is transcripted by mRNA to produce protein according to the information coded in the genome. The produced proteins have functions in living cells. For understanding the activities of genes in a cell, the analysis of produced proteins (expressed proteins) or mRNA are carried out. Especially the analysis of the species and quantities of mRNAs, existing in a cell is important to know the whole figure of the activities and functions of genes.

The analysis of the species and quantities of mRNAs in a cell or tissue is called as gene expression profiling. mRNA is digested easily by ribonuclease (RNase H enzyme) which is in a cell. Therefore, the analysis of mRNA is often carried out by using its complementary strand called cDNA (complementary DNA) which is produced by reverse transcription of mRNA by using a reverse transcriptase.

There are various DNA analysis methods which are used in comparative study of genomes or DNA fragments as well as in gene expression profiling. The gene expression profiling means the analysis of genes working in a cell. Therefore practically it means the analysis of species and quantities of various mRNAs or cDNAs (complementary DNAs which are obtained as the reverse transcription products of mRNAs).

For the comparative analysis of DNAs, gel electophoretic analysis of fragments or DNA sequencing are often used. However, for a long DNA or a DNA mixture, DNA sequencing is not so easy and a simple DNA fragment size analysis is used instead. For the gene function analysis, the gene expression profiling gives an important information. The amount of mRNA in a cell at various environments is analyzed to investigate a correlation between an environment and a gene.

However, this analysis method was very time consuming and labor intensive and it was difficult to get expression profilings of various genes at a time. Recently, various new technologies and instruments have been developed which enables us to detect the gene expressions of many genes. As the present invention is focused more on gene expression profiling, the following explanation is done for the gene expression profiling.

The methods for the new technologies and instruments include the use of DNA chip and DNA fragment scanning. A review of methods for gene expression profiling is described in Nature Biotechnology 14, 1675–1680 (1996).

DNA chip means a DNA probe array on a solid substrate. It has many cells having different DNA probes, respectively. A DNA probe has a specific sequence and can hybridize with a corresponding complementary DNA sequence which appears in a target DNA. In an analysis of mRNAs (or cDNAs) with a DNA chip, cDNAs are prepared from the target sample containing various mRNAs. They are digested with enzymes and then labeled with fluorophore tags. The labeled fragments are hybridized with DNA probes on a DNA chip.

If there are complementary strands of the fragments in the DNA probes, the fragments are hybridized with DNA probes. Even after a washing process for removing unhybridized fragments from the DNA chip surface, the fluorophore labeled fragments complementary to DNA probes can be held on the DNA chip to be detected with a fluorescent microscope. The positions, therefore the probe species of trapped DNA fragments and the amount of the same are detected with a fluorescence microscope.

This method is applied to the gene expression detecting as reported in Proc. Natl. Acad. Sci. USA, 93, 10614–10619 (1996). The DNA chip method is very useful for detecting known genes. However, it is not: suitable for detecting unknown genes because probes for detecting unknown genes cannot be produced without their sequence information.

Another powerful method for detecting a gene expression is the scanning method. The "scanning" means that the method can detect any fragments by size independently from their sequences. It uses a gel electrophoresis. Autoradiography with radio isotope labeling or fluorescence detection is used. The key point of the method is to produce a short DNA fragment which is a part of each DNA in a sample and can be a signature of it by PCR (Polymerase Chain Reaction).

There are several ways for that. Fluorescent Differential Display method (FDD) (FEBS Letters 351, 231–236 (1994)) uses electropherograms of PCR products obtained with a long fluorescent labeled primer and several short arbitrary primers, which may hybridize with several parts of target DNAs, for comparing cDNAs prepared under different conditions.

Molecular index method as well as AFLP (Amplified Fragment Length Polymorphism) (Nucleic Acids Research, 24, 2616–2617 (1996) and Nucleic Acids Symposium Series, 35, 257–258 (1996)) use electropherograms of PCR products obtained sets of long primers which can hybridize to terminal bases of the target fragment DNAs.

In the latter methods, DNAs in a sample are the target for an analysis and are prepared to have special base sequence at 3' (or 5') terminus (being called site A), which will be one of the priming sites in PCR reaction later. As their sizes are various and not adequate for electrophoresis as they are. DNAs are digested by a restriction endonuclease into fragments and the fragments including the site A of the original long DNAs are used as the signature fragments of the DNAs.

The termini of the digested fragments are ligated with a second oligomer which make the another hybridization site (site B) for PCR primers. The both sites A and B are used as the priming sites for PCR amplification of DNA fragments. The products are analyzed to give information of DNA species and abundance (population) of the DNAs in a sample.

The advantage of the scanning method is that any DNA probes specific for individual DNAs are not necessary and therefore it can be applied for detecting unknown DNAs, the DNA probes for which cannot be prepared. It is very powerful and useful to look for new genes, for which the probe cannot be produced in advance. For scanning all the DNAs included in a sample, the latter method has an advantage. The method is described because the present invention has done to improve its drawbacks.

The target is a sample consisting of various cDNAs which represent gene expression. What we want to do is to clarify the DNA species and their relative abundance or population. The best way is to analyze them directly by gel electrophoresis, however, they may be digested at somewhere and they are too long to carry out a precise size analysis. The precise size analysis of DNA fragments by gel electrophoresis can be carried out as far as the sizes are smaller than about 1 kb (1000 bases) in length. They should be digested into small fragments and one fragment of each DNA should be chosen to represent the DNA for the analysis.

This can be done as follows: All the cDNAs in a sample are prepared as a double stranded DNA, one strand of which has a polyA chain (polyA tail) at the 3' termini. As there is only one polyA tail region in each cDNA, a sequence adjacent to the polyA tail region is used as a signature sequence of the cDNA. The cDNA species and their population can be determined by analyzing the fragments containing the signature sequences.

The double stranded cDNAs are digested with an endonuclease and the products are ligated with an oligomer at the termini. The fragments including the polyA tail (site A) and the ligated oligomer (site B) can be amplified by PCR. The PCR amplifications are carried out with an oligo dT primer and the primer having sequences complementary to the ligated oligomer and having one- base sequence or two-base sequence (being called as selective sequences) to distinguish the fragments. When the total number of cDNA species is too large, it will be difficult to distinguish all the fragments by one electropherogram because too many peaks appear in the electropherogram.

The selective sequences are very effective for grouping DNA fragments according to their terminal sequences. Complementary strand extension reactions occur when the primers hybridize perfectly onto the templates (target DNAs). Especially a complete match at 3' terminus of the primers is necessary for the successful complementary strand extension in PCR.

Therefore, the selective sequences are used to selectively amplify a part of the fragments which reduce the number of peaks appearing in one electropherogram. Many electropherograms obtained with a various combination of two selective primers, instead of one electropherogram, are obtained to give a more precise information on the cDNAs (gene expression profilings). When one of the primers is labeled with a fluorophore tag, the electropherogram can be obtained with a fluorescence detection type DNA sequencer.

As the number of genes (therefore cDNA species) acting in a cell is supposed to be over 10,000 and the number of peaks being distinguished easily in one electropherogram is about 100, the number of groups or classification by the selective primers should be over 100. This can be done with the sets of selective primers having two base sequences at the 3' termini. The variations produced from two sets of these primers are 256 (16×16) or 192 (16×12). All the fragments should appear in either of 256 or 192 electropherograms.

SUMMARY OF THE INVENTION

The present invention relates to an analysis method for gene expression profiling and comparative study of DNA fragments in a complex mixture by gel electrophoresis coupled with a laser induced fluorescence detection.

The above-mentioned conventional methods for detecting DNA fragments have drawbacks. The DNA chip (DNA probe array) method cannot be applied to detection of unknown DNAS. Further, it is not so easy to make a DNA chip which one want to use for his special target. On the other hand, the scanning method can overcome this difficulty. However, the sizes of the observable fragments are determined by sequences of the amplified fragments in the scanning method and cannot be controlled artificially.

The grouping is also uncontrollable artificially. Small peaks representing some genes may appear in or be displayed in the same electropherogram where big peaks appear at the position near the small peaks. In such a case, the detection and quantification of the small peaks are very difficult. This is one drawback of the scanning method. Sometimes one wants to detect only a part of the expressed genes.

Further, the scanning method cannot select the genes and undesirable peaks appear in an electropherogram, which make the situation complicated. It would be also very convenient if the cDNA fragments caused by unknown genes are separately detected in an electropherogram. This is a big subject to be solved, which the conventional methods including the DNA chip and the scanning methods cannot solve.

In addition, the scanning method is very powerful and useful for gene expression profiling as well as comparative study of DNA fragments. However, it has a drawback in applying it to complex fragments mixture. The grouping of the fragments is carried out by their terminal base sequences adjacent to the restriction enzyme recognition site and is not artificially controlled. Even if there are several peaks which are desired to be displayed in one electropherogram, they may be displayed separately. In some case the reverse case may occur.

To overcome the above mentioned difficulty, specific primers and common primers are used in PCR. The specific primers of 15–30 mers, which are specific to individual target DNAs and complementary to them, respectively, and the common primers which hybridize with all or some of DNAs in a sample. The specific primers select the fragments which should be differently detected from the others. The common primers are used to amplify all the fragments in the group.

Both of the specific primers and the common primers may be labeled with different fluorophores, respectively, to distinguish them each other. In some case, the common primers may not be labeled, then only the specific fragments produced with the specific primers through PCR reactions can be detected. The primers are used in PCR reactions, the products of PCR reactions are used to obtain electropherograms of the fragments.

This method is successfully applied to detecting gene expression profilings, wherein the fragments from the known genes are amplified with the non-labeled common primers and the specific primers which are labeled, for example, with fluorophore 1, and the other fragments mainly from unknown genes are amplified just with sets of the common primers, one of which is labeled with fluorophore 2 which has a different emission wavelength from fluorophore 1. The both of these PCR products are separately detected in a gel electropherogram.

Consequently, the gene expression from the known genes and that from unknown genes are detected simultaneously and separately. One of the practically important applications is to classify and detect expressed genes by their expression level, which may proportional to the copy numbers of mRNA, therefore to the copy numbers of the amplified fragments.

It would be good for detecting various kinds of genes to make the peak heights appearing in an electropherogram at the same size. If the strongly expressed genes are labeled with a fluorophore emitting weak fluorescence and the weakly expressed genes are labeled with a fluorophore emitting strong fluorescence, the observed peak heights in an electropherogram may come to the same height region. Of course, the color filter transmission efficiency can be controlled for that instead of changing the emission yield of the fluorophore.

Another important application of this invention is to classify and label DNA fragments according to their corresponding gene functions. Usually a gene cascade reaction occurs when an external stimulation is given to a cell. There are closely related gene groups (families) in the reaction cascades. It is very convenient to understand gene functions and the information transfer pass way that each closely related gene group (family) is labeled with its identical fluorophore. The DNA fragments in different gene groups are easily distinguished in color.

The above-mentioned differential labeling can be carried out as follows. The target DNA fragments are prepared as the same way as that in AFLP or other scanning methods. As the target fragment DNAs have been ligated with oligomers at their termini to have priming sites for PCR, all the fragments can be amplified with a set of common primers (primer I of primer set I and primer II of primer set II) which can hybridize with the oligomer sequences at the termini of all the fragments. If one of the primer (for example, primer I) is labeled with a fluorophore (fluorophore I), the PCR products will be labeled with the fluorophore as well.

Any DNA fragment can be distinguished in color or fluorescence from others by using a specific PCR primer. The specific PCR primer has a complementary sequence to a part of the target DNA sequence and can hybridize with it. As it is labeled with another fluorophore (fluorophore III), the product can be easily distinguished from the products of the common primers. When the specific primer (primer III) hybridizing with a fragment in the PCR mixture is added to the mixture containing primers I and II, a PCR product having a shorter length than the length of that produced with primers I and II, is produced by a reaction with primer III and primer II. As a result, shorter products become dominant in a competitive PCR reaction.

As the specific primer is labeled with another fluorophore (fluorophore III) and the product has fluorophore III, it can be easily distinguished in color from others.

The primers specific to the targets can be prepared when the target sequences are known. The sequence of the specific primers is designed so as to hybridize with the target at their middle position. Competitive PCR reactions occur between PCR by the primer I of the primer set I and the primer II of primer set II, and PCR by the primer II of the primer set II and primer III. In a competitive PCR reaction, a reaction giving small fragments becomes dominant.

Therefore, the product by primers II and III can be the major product in the reaction. This means that we can control a product DNA length by adding a primer III hybridizing specific to the target DNA, while the other fragments originated in the unknown DNA fragments or other than the specific target DNAs are produced by primers I and II.

The above example explains the case in which the sequence-known DNA fragments are distinguished by labeling special fluorophore from the sequence-unknown DNA fragments produced by common primers (primers I and II).

This differential labeling method is also applied to distinguish several different DNA fragment groups such as house keeping genes, genes specific to organs such as brain, liver, skin, intestine, stomach, cancer cells, spleen and the like.

The samples include genomic DNAs or cDNAs produced by reverse transcription from mRNA of the above-mentioned tissues or cells. In the case of genomic DNA analysis, the size of DNA is so long and it is digested by enzymes such as class II endnucleases or class IIS endonucleases. They include EcoR I, Pst I, Hha I, Nla III, BspM I, Fok I, etc. The enzymes are listed in Molecular Cloning (1989), 5.3–5.8 (Restriction and DNA Methylation Enzymes).

An oligonucleotide having known base sequence of from 10 to 30 bases (10 mer to 30 mer), desirably from 15 mer to 25 mer, is ligated to at least one of the strands of a DNA fragment at its 3' terminus. As the oligonucleotide part is used as a priming part in PCR or complementary strand extension, the following sequences are conveniently used.

GTTTTCCCAGTCACGAC (SEQ ID NO.1)
CAGGAAACAGCTATGAC (SEQ ID NO.2)
ATTAACCCTCACTAAAG (SEQ ID NO.3)
AATACGACTCACTATAG (SEQ ID NO.4)
CGAGGTCGACGGTATCG (SEQ ID NO.5)
TCTAGAACTAGTGGATC (SEQ ID NO.6)
TCTCCAAAAAAAAAAAAAAA (SEQ ID NO.7)
TGTGGTTTTTTTTTTTTTTT (SEQ ID NO.8)

When a class IIS endonuclease such as Fok I, BspM I, BsmA I, BsmF I, etc., is used to digest a DNA, single stranded termini are produced, which are called cohesive termini. The length of a cohesive terminus is usually several bases long depending on the enzyme. The ligation adapter having a known sequence is ligated at 5' terminus (cohesive termini) of digested fragment.

When the base sequence of the extended portion of the oligomer is not complementary to the cohesive termini of the digested fragment, the ligation reaction cannot be carried out. This characteristic of the selective ligation can be used to classify the digested fragments into groups.

Now we have a DNA fragment group or fragment groups which have the same terminal base sequences and selective sequences of 1 to 4 bases adjacent to terminal base sequences, if necessary.

The fragment groups with the target DNA sample and with the standard DNAs are compared. All the fragments can be amplified by PCR with primers I and II which can hybridize to the ligated oligomer part of fragments. If the number of fragment species in a group is too large, the fragments are divided into many groups through PCR with selective primers which have the common sequence hybridizing with the common part of the ligated oligomer and the selective sequences adjacent to it.

For the comparison of the target sample and standard one, their electropherograms are obtained. If the number of DNA fragment peaks appearing in an electropherogram is very large, it will be not good for an accurate comparison of them. In such a case. The number of fragment species in one fragment group should be reduced.

The reduction of the number of fragments is carried out by using the above-mentioned selective primers having the selective sequence part of from 1 to 4 base sequences. Only fragments hybridizing with the PCR primers can be amplified and therefore appear in an electro-pherogram. Instead of the reduction of the appearing peak number, many electropherograms corresponding to various pairs of selective primers are required for the precise analysis.

This is successfully carried out, however, the grouping is determined by their terminal base sequences and it cannot be controlled. Fragments originated in a gene being strongly expressed in a cell may appear as big peaks in an electropherogram where fragments produced from a target or an important gene appear in the same region of the electropherogram and the fragments cannot be detected separately at the region near the big peak. It must be very convenient to make a fragment group in which all the fragments appear with almost equal intensities.

In another case, the fragments, corresponding genes of which are closely related to each other in a cell, should be appear in an electropherogram for a comparative study. This type of rearrangement of the grouping of fragments is carried out by using a third primer (primer III).

The third primer has a sequence just specifically complementary with a specific fragment, therefore it can only hybridize with one (in some cases several) fragment. The presence of the primer III in a PCR reaction together with primers I and II makes the PCR product corresponding to a fragment shorter than that produced with primer I and II.

This invention provides a reagent kit which contains at least a pair of the terminal selective primers having common sequence and selective sequence or a pair of primers having common sequence, and a specific primer having specific sequence. Of course a plural of the specific primers having sequences complementary to specific or individual fragments can be used instead of one specific primer according to the purpose.

In any case the products of the third primers (specific primers) give controlled fragment sizes which are good for measurement by gel electrophoresis. The kit has various sets of primer pairs or primers, and various specific primers.

To sum up, a DNA fragment preparation method for DNA analysis and a reagent kit used in the DNA fragment preparation method in this invention include methods and kits which are described as follows.

(1) The DNA fragment preparation method for DNA analysis comprising:
  i) preparing a plurality of DNA fragments from a sample DNA; and
  ii) amplifying a specific DNA fragment by PCR, using a pair of primers (identical primers or common primers) which hybridize with terminus sequences of the DNA fragments, and a specific primer which hybridizes specifically with a base sequence of the specific DNA fragment at a position between a priming site of one primer of the pair of primers and a priming site of another primer of the pair of primers (the specific primer hybridizes specifically with a base sequence at a middle position of the specific DNA fragment).

(2) The DNA fragment preparation method for DNA analysis according to (1), wherein at least one primer in the pair of primers and the specific primer is labeled with the fluorophore.

(3) The DNA fragment preparation method for DNA analysis according to (1), wherein a labeling material labeling the pair of primers is different from a labeling material labeling the specific primer.

(4) The DNA fragment preparation method for DNA analysis according to (1), wherein a labeling material labeling the pair of primers is different from a labeling material labeling the specific primer, and the label labeling the specific primer is a fluorophore.

(5) The DNA fragment preparation method for DNA analysis according to (1), wherein a labeling material labeling the pair of primers is different from a labeling material labeling the specific primer, and the label labeling the specific primer is biotin.

(6) The DNA fragment preparation method for DNA analysis according to (1), wherein an oligomer having known base sequence is connected to at least one terminus of the DNA fragments, and one primer of the pair of primers hybridizes with the oligomer.

(7) The DNA fragment preparation method for DNA analysis according to (1), wherein an oligomer having known base sequence is ligated at least at one terminus of the DNA fragments by ligation reaction, and one primer of the pair of primers hybridizes with the oligomer.

(8) The DNA fragment preparation method for DNA analysis according to (1), wherein a polyA sequence is connected to at least one terminus of the DNA fragments, and one primer of the pair of primers hybridizes with the polyA sequence.

(9) The DNA fragment preparation method for DNA analysis according to (1), wherein an oligomer having known base sequence is connected to at least one terminus of the DNA fragments, and at least one primer of the pair of primers has a base sequence complementary to a base sequence of the oligomer and a variable (or arbitrary or selective) sequence of 1 to 4 bases at 3' terminus to discriminate a base species of 1 to 4 bases at 5' terminus of the DNA fragments to be amplified by PCR, the 1 to 4 bases are selected from the group consisting of A, T, G and C.

(10) The DNA fragment preparation method for DNA analysis according to (1), wherein an oligomer having known base sequence is connected to at least one terminus of the DNA fragments, and at least one primer of the pair of primers has a base sequence complementary to a base sequence of the oligomer and a variable (or arbitrary or selective) sequence of 1 to 4 bases at 3' terminus to discriminate a base species of 1 to 4 bases at 5' terminus of the DNA fragments to be amplified by PCR, the 1 to 4 bases are selected from the group consisting of A, T, G and C, and wherein the variable sequence is directly adjacent to 3' terminus of the base sequence complementary to the base sequence of the oligomer, a part of bases including the base sequence complementary to the base sequence of the oligomer is replaced by a nucleotide analogue or a mismatched nucleotide to give much serious effect on a complementary strand extension of at least one primer of the pair of primers.

(11) The DNA analysis method comprising:
  i) preparing a plurality of DNA fragments;
  ii) amplifying a specific DNA fragment by PCR, using a pair of primers (identical primers or common primers) which hybridize with terminus sequences of the DNA fragments, and a specific primer which hybridizes specifically with a base sequence of the specific DNA fragment at a position between a priming site of one of primer the pair of primers and a priming site of another primer of the pair of primers (the specific primer hybridizes specifically with a base sequence at a middle position of the specific DNA fragment); and
  iii) separating, by electrophoresis, DNA fragments labeled with fluorophore produced in step ii), and detecting fluorescence emitting from the fluorophore.

(12) The DNA analysis method according to (11), wherein each of the pair of primers has a common sequence (which is common or identical to the pair of primers) and a variable sequence of 1 to 2 bases at 3' terminus, to discriminate a base species of 1 to 2 bases at 5' terminus of the DNA fragments to be amplified by PCR, the 1 to 2 bases are selected from the group consisting of A, T, G and C, and wherein electropherograms of DNA fragments produced in step ii) by use of the pair of primer and the specific primer are obtained, and the electropherograms are obtained for all possible combinations 1 to 2 bases of the variable sequences of the pair of primers.

(13) A reagent kit comprising:
a pair of primers, wherein each of primer of the pair of primers has a common (or identical) to the pair of primers and hybridizes with terminal sequences of DNA fragments prepared from a sample DNA; and
specific primers which hybridize specifically with a target DNA fragments to be amplified by PCR using the pair of primers alone, wherein the specific primers control lengths of products of PCR.

(14) A reagent kit comprising:
a pair of primers, wherein each of primer of the pair of primers has a common (or identical) to the pair of primers and a variable (or arbitrary or selective) sequence of 1 to 4 bases at 3' terminus to discriminate a base species of 1 to 4 bases at 5' terminus of the DNA fragments to be amplified by PCR, the 1 to 4 bases are selected from the group consisting of A, T, G and C, and wherein each of primer of the pair of primers hybridizes terminal sequences of DNA fragments prepared from a sample DNA; and specific primers which hybridize specifically with a target DNA fragments to be amplified by PCR using the pair of primers alone, wherein the specific primers control lengths of products of PCR.

(15) A reagent kit comprising:
a pair of primers, wherein each of primer of the pair of primers has a common (or identical) to the pair of primers and a variable (or arbitrary or selective) sequence of 1 to 4 bases at 3' terminus to discriminate a base species of 1 to 4 bases at 5' terminus of the DNA fragments to be amplified by PCR, the 1 to 4 bases are selected from the group consisting of A, T, G and C, and wherein each of primer of the pair of primers hybridizes terminal sequences of DNA fragments prepared from a sample DNA; and
specific primers each of which hybridizes specifically with a base sequence of the specific DNA fragment at a position between a priming site of one primer of the pair of primers and a priming site of another primer of the pair of primers (the specific primers each hybridizes specifically with target DNA fragments at middle positions of the target DNA fragments to be amplified by PCR using the pair of primers alone), wherein the specific primers control lengths of products of PCR.

The present invention is very useful to distinguish and display DNA fragments of genes according to their characteristics such as whether they are known or unknown, and strongly expressed in a cell or not, and the like. The usefulness is increased when the differently classified fragments are differently colored by fluorophore tagging. They are separately detected with a color selective detector.

DESCRIPTION OF THE PREFERRED EMBODIMENTS

The followings are the embodiments of the present invention.

EMBODIMENT 1

Figure 1:
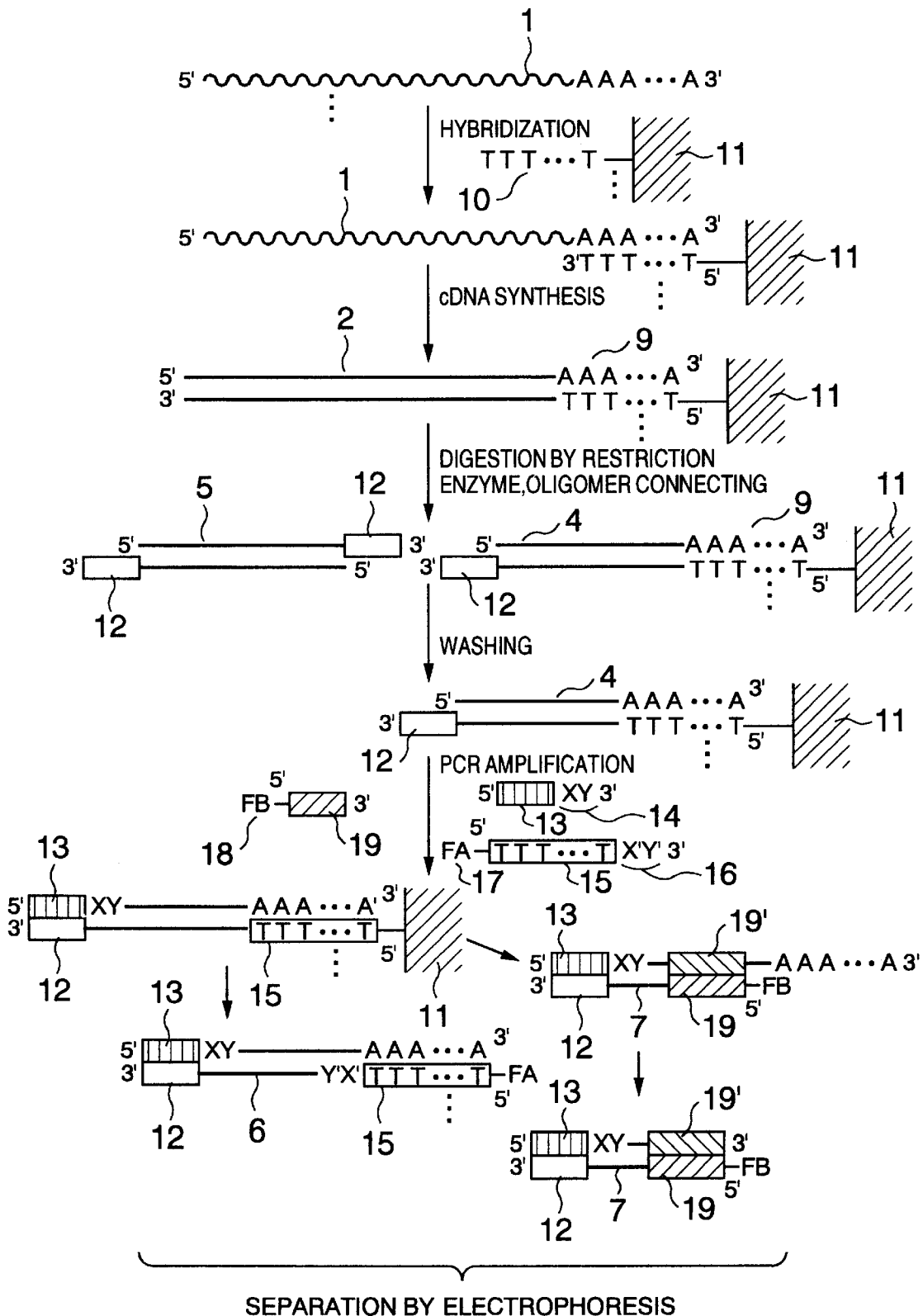
FIG. 1 illustrates a procedure to detect expressed genes in a cell according to the present invention which is precisely figured out in Embodiment 1.

The flow of the procedure of obtaining DNA fragments from a sample containing various mRNAs is illustrated in FIG. 1. A titerplate 11 immobilizing polyT strand 10 on the surface is used to trap (capture) mRNAs 1 in the sample solution. Complementary strand extension reactions from polyT oligomers are carried out to produce double stranded cDNA 2. In the embodiment 1, the production of double stranded cDNAs 2 are produced on a surface of the titerplate, but it can be done in a liquid phase followed by trapping on a surface of a solid support.

The double stranded cDNA 2 is digested by a restriction endonuclease and then the known oligomer 12 (this means the sequence of the oligomer is known) is ligated to the terminus. There are two types of fragments (numerals 4 and 5). The first one is the fragment 4 bound to the surface of the titerplate and have the oligomer 12 at one end and polyA sequence at the other end. The second one is the fragment 5 in a reaction solution and has oligomers 12 at both ends.

The fragments 5 in a solution are washed out. Thus, only fragments 4 having polyA terminus and oligomer sequence terminus are obtained. It can be considered that the fragments represent the corresponding mRNAs. Therefore the species and the amount of their cDNA fragments (numeral 4) mean the gene expression profiling of the cell or cells being investigated.

As the copy numbers of the fragment species are usually very small to be detected by the fluorescent DNA sequencer or the gel electrophoresis with the other detection methods, they are amplified before the detection. When a large number of cDNA fragment species are in a sample, the electropherogram may have so many peaks in it that they cannot be separately detected. The electropherogram may be like smear.

To avoid this difficulty, the fragments are classified into several groups which contain not so many fragment species and therefore not so many peaks in an electropherogram.

To classify the fragments, the primers having selective two base sequences are used in PCR amplification. Only fragments which have the sequence matched with the primers can be amplified in the PCR reaction. The primer II (numeral 13) (primer of pair of primers) of primer set II has the complementary sequence to the ligated oligomer (numeral 12) and two-base sequence XY (X and Y represent either of A, T, G or C) (numeral 14) which is one of the possible 16 two-base sequences. Therefore the primer set II consists of 16 of primer II.

The primer I (numeral 15) (primer of pair of primers) of primer set I has the polyT sequence and two-base sequence X'Y' (X' represents either of A, G or C, and Y' represents either of A, T, G, or C) (numeral 16) at the terminus. The primer I hybridizes with the polyA sequence of a fragment. As the second terminal base is selected from three base species except for T and the terminal base species (the first terminal base) is selected from four of the nucleotide species, there are 12 choices to select the primer I. The primer set II consists of 16 primers and the primer set I consists of 12 primers.

All the combinations of these primers give the possible pair of primers of 192 which are used to classify and amplify the fragments. As each PCR product is analyzed by electrophoresis, the number of electropherograms required for obtaining an expression profiling is 192 in this embodiment.

Figure 2:
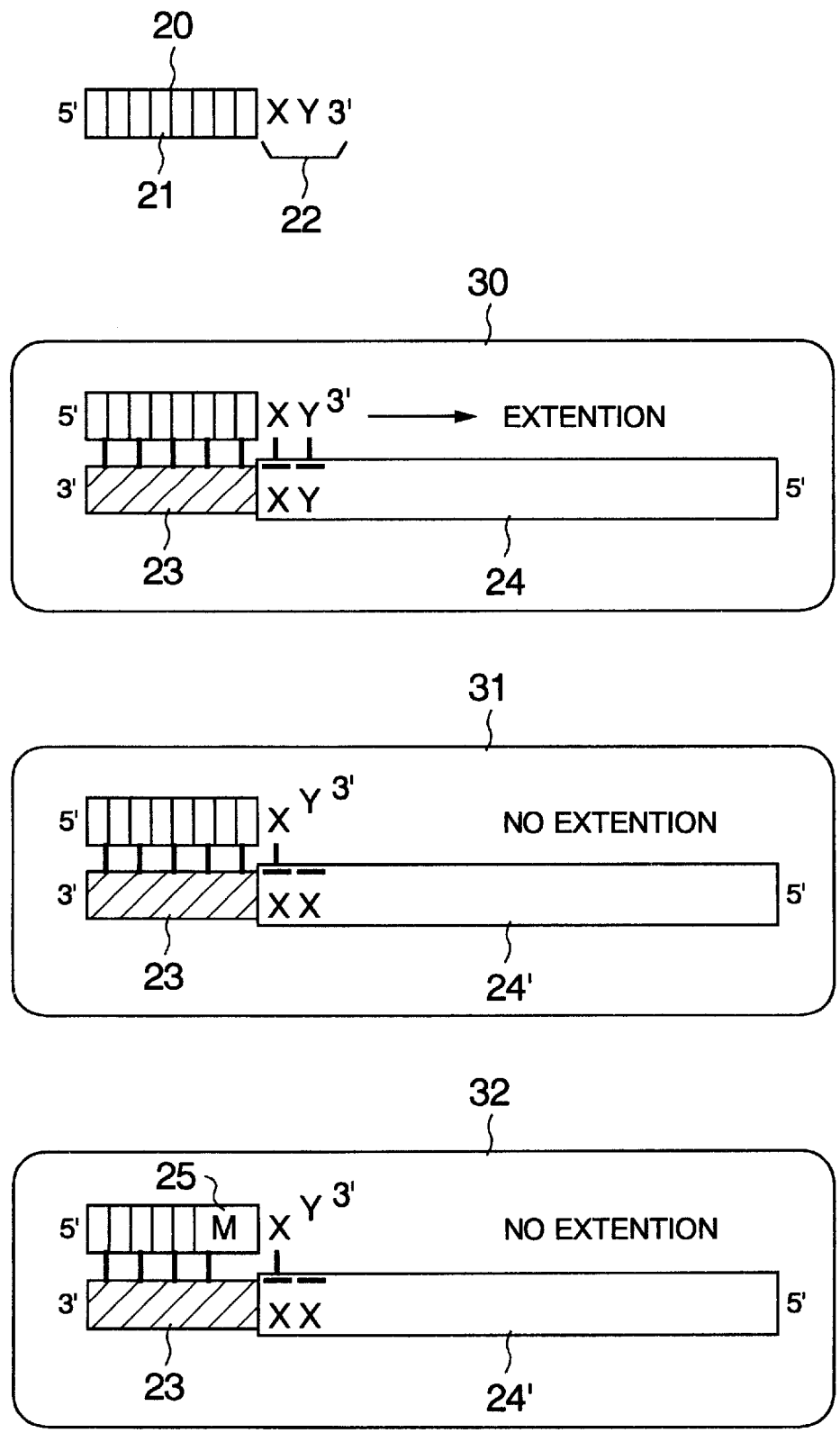
FIG. 2 is a schematic diagram illustrating the complementary strand extension reactions which depend on whether the terminal sequences of primers hybridize with the target fragments perfectly or not, in Embodiment 1.

As mentioned above, a set of selective primers are used in PCR to obtain a fragment group. FIG. 2 is a schematic diagram illustrating the complementary strand extension reactions which depend on whether the terminal sequences of primers perfectly hybridize with the target fragments or not.

The primer I or II (numeral 20) has the common sequence (numeral 21) complementary to the oligomer 23 ligated to the DNA fragment 24 and the selective two-base sequence XY 22 at the 3' terminus.

The complementary strand extension from the primer occurs in the case (numeral 30) that the terminal two-base sequences hybridize with the fragment perfectly. XY of primer 20 hybridizes with $\overline{XY}$ of the DNA fragment 24.

On the contrary, as shown numeral 31 and 32, when XY of primer 20 does not hybridize with $\overline{XX}$ of the fragment 24', the mismatch in the terminal two-base especially at the 3' terminal base species of the primer prevent or reduce the complementary strand extension.

Of course the mismatched primers sometimes extend their strand, although it is dependent on the mismatched base species. To prevent the extension of the mismatched primer, an artificial mismatch (numeral 25) at the nucleotide adjacent to the selective two-base sequence of the primer 20 can be introduced, where the mismatch in the selective sequence part becomes more serious for the complementary strand extension.

A set of primers for a PCR reaction are from one in the group II (numeral 13) and another in the group I (numeral 15) (FIG. 1). The primers in group I which have polyT sequence and the selective sequences X'Y' are labeled with fluorophore FA 17. The PCR products which have fluorophore FA are analyzed by gel electrophoresis to analyze the fragment lengths and their quantities from the migration speeds and the fluorescent intensity, respectively. The fragments having polyA sequence at 3' termini can be analyzed with this method.

The fragments appear in the electropherograms determined by their sequences. Each fragment has its respective characteristic position in the electropherogram. In some cases, two fragment species may come to the same position in the electropherogram, which is not good for the precise and accurate analysis. This is overcome by shifting the position of at least one of the peak appearing the same position in the electropherogram.

The present invention realizes shifting the position of at least one of the peak by using the primer III (numeral 19) (the specific primer) in addition to primer I and primer II as a pair of PCR primers. The primer III has a complementary sequence to a target fragment, and has fluorophore tag FB 18 at 5' end. Basically it can hybridize to one fragment, of course, it can be made so as to hybridize with several fragments. If the primer III together with the primer I and II is added to the sample for PCR amplification and the primer III hybridizes with the same fragment that the primer I hybridizes with, the fragments shorter than the PCR product by the primer I and II are produced by the PCR with the primer III and II.

Figure 3:
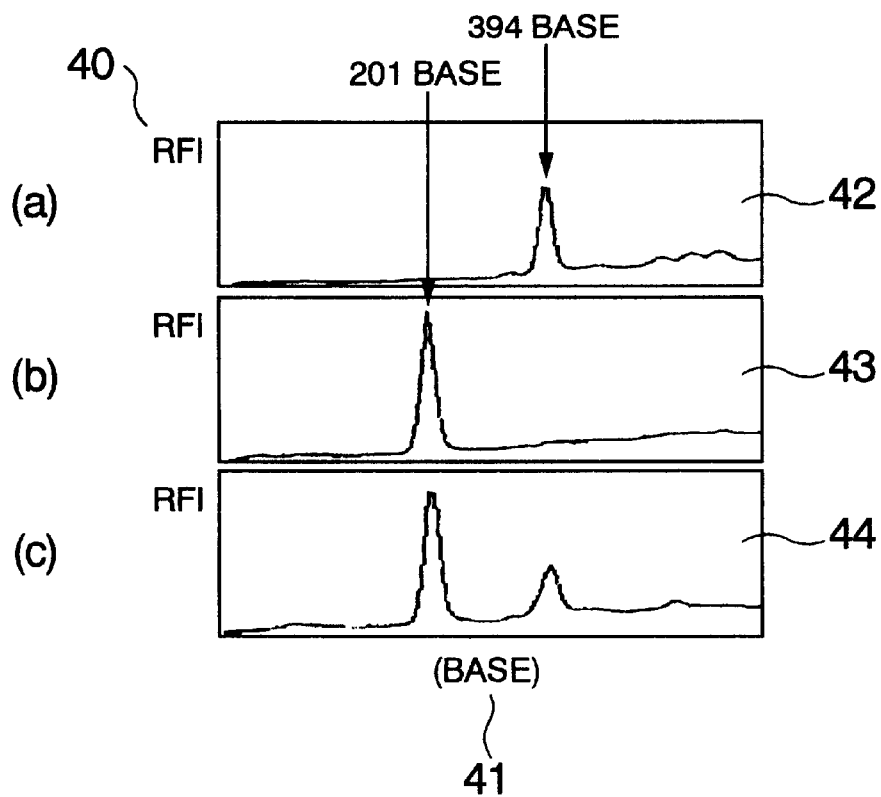
FIG. 3 illustrates PCR products with primers I, II and III. A short product becomes dominant when there are both of a short product and a long product being produced from a PCR reaction with the same template DNA fragment, in Embodiment 1.

The base lengths of these primers are desired to be between 15 and 30 mer. In PCR reactions, if the competitive reactions occur among primers, the shorter product becomes dominant. The shorter product cannot be a template for producing a long product but the long product can be a template of a short product in the PCR process. FIG. 3 illustrates this phenomenon.

In FIG. 3, the vertical axis represents the relative fluorescent intensity (numeral 40) and the horizontal axis represents the base length (numeral 41) of the products. In case (a) (numeral 42), the product is produced from the primers I and II, which gives a long product of base length 394. In case (b) (numeral 43), the PCR product with the primers II and III is displayed. In case (c) (numeral 44), the PCR product with the primers I, II, and III is displayed. The product of 201 bp, which is the product with the primers II and III, becomes dominant.

This means that if the primer III (numeral 19) is labeled with the fluorophore FB 18 different from that used to the fluorophore FA 17 of the primer I (numeral 15), the known fragments can be detected separately from the unknown fragments. This is very useful to look for the fragments related to new genes.

In FIG. 1, numeral 19' denotes base sequence complementary to the base sequence of the primer III, and the base sequence complementary to the base sequence of the primer III is placed between the base sequence XY and polyA sequence at 3' end of the one strand of the DNA fragment.

By the procedure illustrated in FIG. 1, as a result, DNA fragments 7 being amplified by the primer II and III and having a shorter length than DNA fragments 6 being amplified by the primer I and II are obtained.

Figure 4:
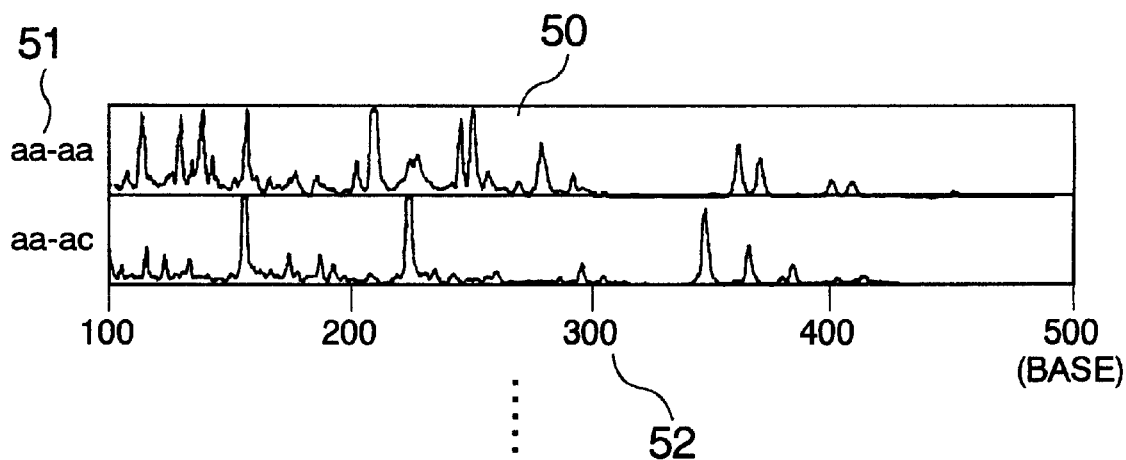
FIG. 4 is a part of electropherogram obtained with a method explained in Embodiment 1.

FIG. 4 is a part of electropherogram obtained in Embodiment 1. In the electropherograms in FIG. 4, numeral 51 denotes the combination of the selective sequence of the primer I and the selective sequence of the primer II for obtaining the electropherograms, and numeral 52 denotes the base length. The electropherograms corresponding to the number of the possible primer pairs (that is, the number of combination of the primer I and II) are obtained. Therefore, the number of the electropherograms is 192 in this embodiment. Only a part of the results are shown in FIG. 4.

The gel electrophoresis system type of real time fluorescence detection is used in this embodiment. There are several possible gel electrophoresis systems, which include a slab gel electrophoresis, a capillary gel electrophoresis and a capillary array gel electrophoresis. Usually various peaks having different peak heights are observed in the electropherograms. As mentioned previously, a peak may be hidden under a big peak. In such a case, the big peak can be shifted and labeled with a low emission fluorophore by using the primer III in PCR.

In other method, this overlapping difficulty is overcome by classifying the products with the further PCR with the primers having the additional selective sequences added to the original selective sequence of two-base at the 3' termini. The number of bases of additional selective sequence can be one to three bases.

Figure 5:
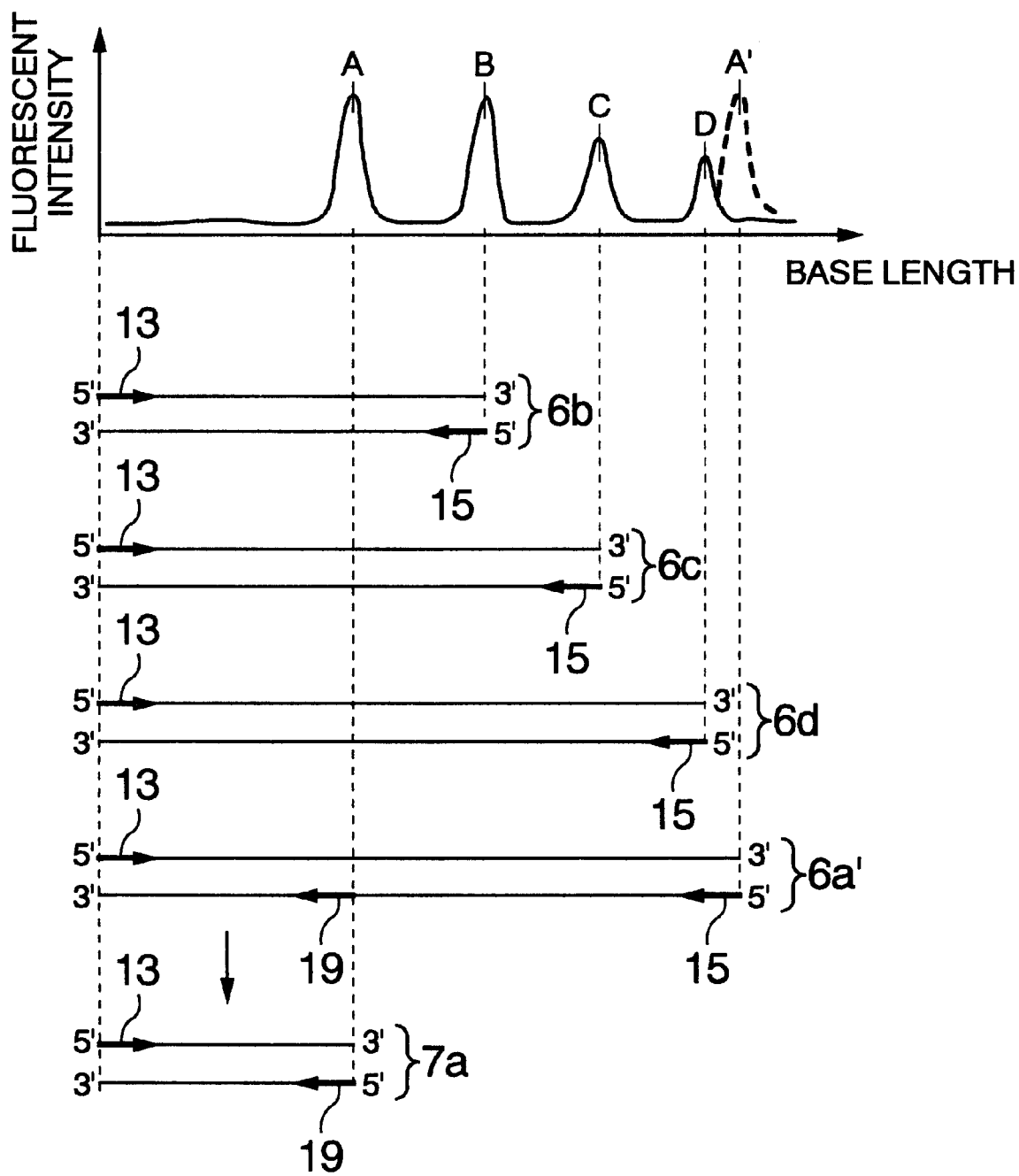
FIG. 5 shows a relation between the shorter fragment production in a competitive PCR and the electropherogram, in Embodiment 1.

FIG. 5 shows the example of the electropherogram obtained from the competitive PCR with the primers I, II and III. Four fragments (numerals 7a, 6b, 6c and 6d) as denoted by A, B, C and D are produced by the PCR in this embodiment as shown in FIG. 5.

In FIG. 5, peak A is originated in the fragments produced by PCR with the primer II and the primer III, and peaks B, C, D and A' are originated in the fragments produced by PCR with the primer I and the primer II.

The peak A does not appear when the primer III (numeral 19) is not used. When the primer III (numeral 19) is not used, the peak A' will appear in the electropherogram instead of the peak A. In that case, the position of peak A' is very close to the peak D. It is very difficult to detect the peaks A' and D separately, but it is overcome by the peak shift by using the primer III to the reaction mixture and shifting the peak A' to the position of peak A.

The primer II (numeral 13) and III (numeral 19) hybridize with the fragment denoted as numeral 6a' in FIG. 5 and produce the short fragment 7a by the PCR reaction. Although sometimes the peak A' is still observed in the electropherogram, the intensity is very weak compared with that obtained without the primer III. When the big peak is originated in the unknown gene, the primer III cannot be prepared in advance.

However, as the big peak or DNA band can be easily taken out by cutting the DNA band from the gel and is sequenced. Then the primer III (numeral 19 ) for the big peak can be designed and produced by oligonucleotide synthesis.

As the primer I (numeral 15) which hybridizes with the 5' end of fragments (numerals 6b, 6c and 6d), and the primer III (numeral 19) which hybridizes with the fragment (numerals 6a' and 7a), are labeled with fluorophores, they are observed in the electropherogram. If the primer III is only labeled with a fluorophore, the known and shortened fragment is the only product observed in the electropherogram.

On the other hand, the primer III is not labeled and the primer I is labeled with a fluorophore, only fragments originated in the unknown genes are observed in the electropherograms. The method can be applied not only to observe the electropherograms but also to fractionate the target DNA fragments.

As mentioned above, only fragments originated in the unknown genes can be separately detected The capillary gel electrophoresis instrument having the sorting and collecting unit has been already developed (Japanese Patent Application Laid-Open No. 174693/1994 and No. 181164/1995). The signal from the DNA fragments are monitored, and when the signal is bigger than the determined threshold, the fragment is sorted and fractionated in a sampling tray. This is very useful for gene hunting.

EMBODIMENT 2

Figure 6:
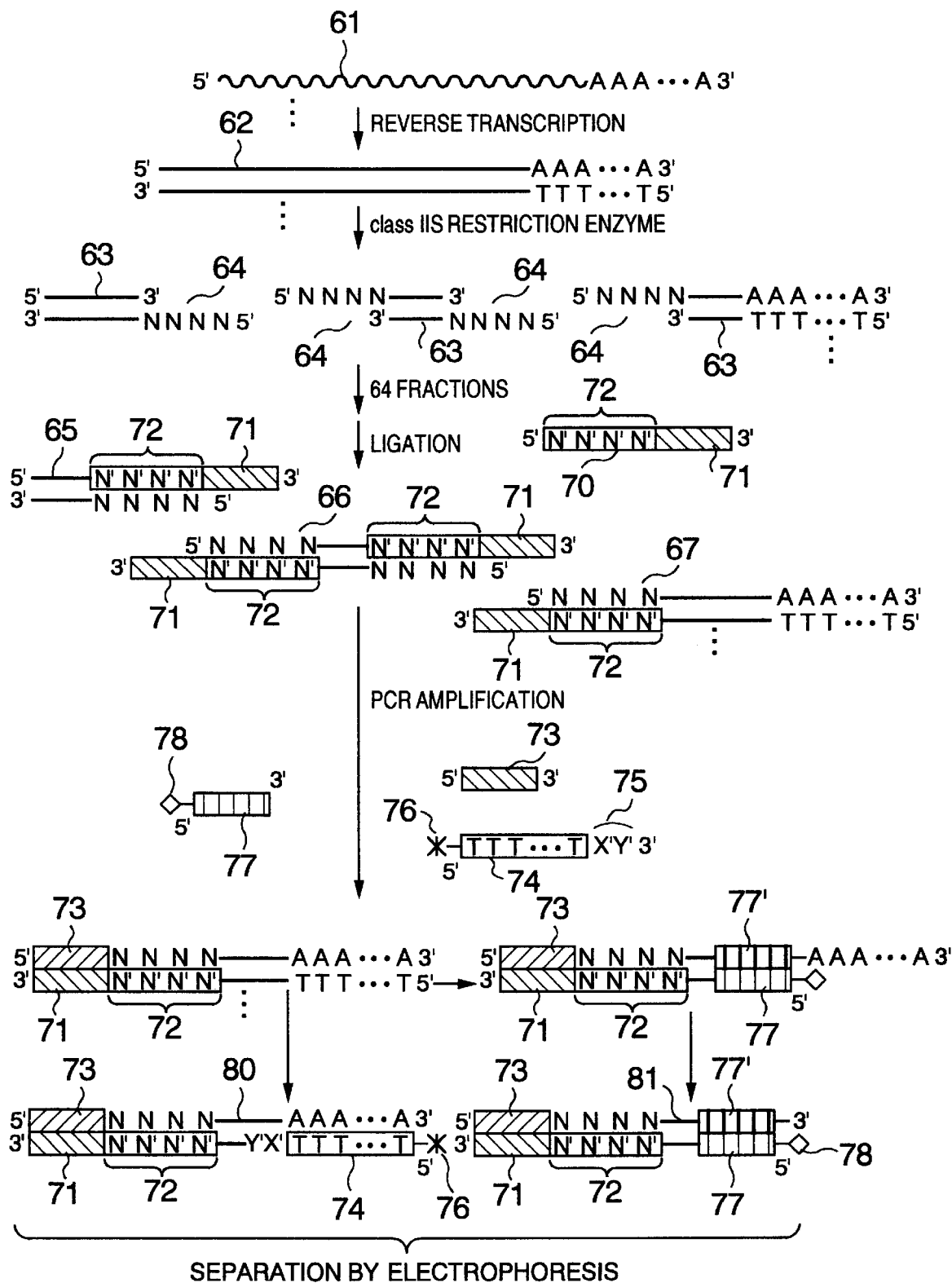
FIG. 6 shows the flow of the sample preparation in the molecular index, in Embodiment 2.

This embodiment uses another DNA fragment preparation method, so-called molecular index. The flow of the sample preparation in the molecular index is shown in FIG. 6.

Double stranded cDNAs 62 are produced by the reverse transcription from mRNA 61. They are digested into small fragments 63 by the class IIS endonuclease. The class IIS endonuclease digests DNAs at a position different from the recognition sequence and usually produces the cohesive end of several oligonucleotides, the sequences of which are individual sequences to the fragments as noted by NNNN (numeral 64) in FIG. 6. N represents either of A, T, G or C.

The oligomers 70 having a base sequence complementary to the cohesive end 64 are ligated to the fragments 63 to obtain fragments (numerals 65, 66 and 67). The oligomers 70 have the identical (or common) sequence part 71 of 15–30 bases and the variable (or arbitrary or selective) sequence part of 4 bases (numeral 72).

The sequence of the variable (or selective) parts 72 can be any four (4) base sequences, which is used to select the fragment, to which the oligomer is ligated. The variable (or arbitrary or selective) part of the terminal sequence of the oligomers change according to the type of the enzyme used. When the length of the variable (or arbitrary or selective) part is 4 as in this embodiment, the number of the sequence variation is 256.

The DNA fragments can be classified or grouped into 256 at maximum with 256 different oligomers. The number of groups can be reduced by using the oligomers having the terminal sequence form of (A+C+T+G) N'N'N' (N' represents either of A, T, G or C). Where (A+C+T+G) means that the oligomer is a mixture, the forth nucleotide from the 3' termini of which is the mixture of A, C, T and G. Now the number of groups is reduced to 64. That is, the mixture of oligomers each having known sequence (AN'N'N', TN'N'N', GN'N'N' and CN'N'N') as the variable (or arbitrary or selective) sequence part (numeral 72) is used as the oligomers 70 of the oligomer set including 64 oligomers.

The reaction mixture is divided into 64 fractions and one of the oligomers is added to each fraction (In FIG. 6, only one fraction is shown), respectively, for carrying out ligation reactions. The ligation reaction occurs only when a variable sequence part of the oligomer completely hybridizes with the cohesive end of DNA fragment.

The oligomer ligated fragments (numeral 67) are templates for PCR reactions. The ligated fragments in each fraction are amplified with the primer II (numeral 73) (primer of pair of primers) and primer I (numeral 74) (primer of pair of primers) of the primer set I. The primer II hybridizes with the identical (or common) sequence part 71 of the oligomers 70. The primer I of the primer set I has the polyT sequence at the 5' terminus and the variable (or arbitrary or selective) sequence (numeral 75) consists of one or two base sequence (X' or X'Y', where X' represents either of A, G or C, and Y' represents either of A, T, G or C) at the 3' terminus. The primer set I consists of 12 primers as Embodiment 1.

The primer I is labeled with a fluorophore 76 (*) so that a longer fluorophore labeled PCR product (numeral 80) is obtained. The PCR products are analyzed with a fluorescent gel electrophoresis analyzer or fluorescent DNA sequencer. The above method can analyze all the fragments produced from mRNA.

As there are so many mRNA species in a tissue or a cell, several fragments in a group may have lengths close to each other. The peak position in the electropherogram has to be shifted for detecting these separately. The primer III (numeral 77) (specific primer) labeled with the fluorophore 78 (◇) different from the fluorophore (*) is added to the reaction mixture. The primer III can hybridize with the fragment at a position between the priming sites of the primers I and II.

As mentioned before, the shorter product 81 becomes dominant in the competitive PCR, the product of PCR with the primer III and the primer II become the major product, which is labeled with fluorophore 78 (◇) different from fluorophore 76 (*). In FIG. 6, numeral 77' denotes a base sequence complementary to the base sequence of the primer III.

The longer products by PCR with the primer I and the primer II are easily distinguished from the shorter products by PCR with the primer II and the primer III. Similarly to Embodiment 1, the fragments originated in the unknown genes can be detected separately from those of known genes.

EMBODIMENT 3

Figure 7:
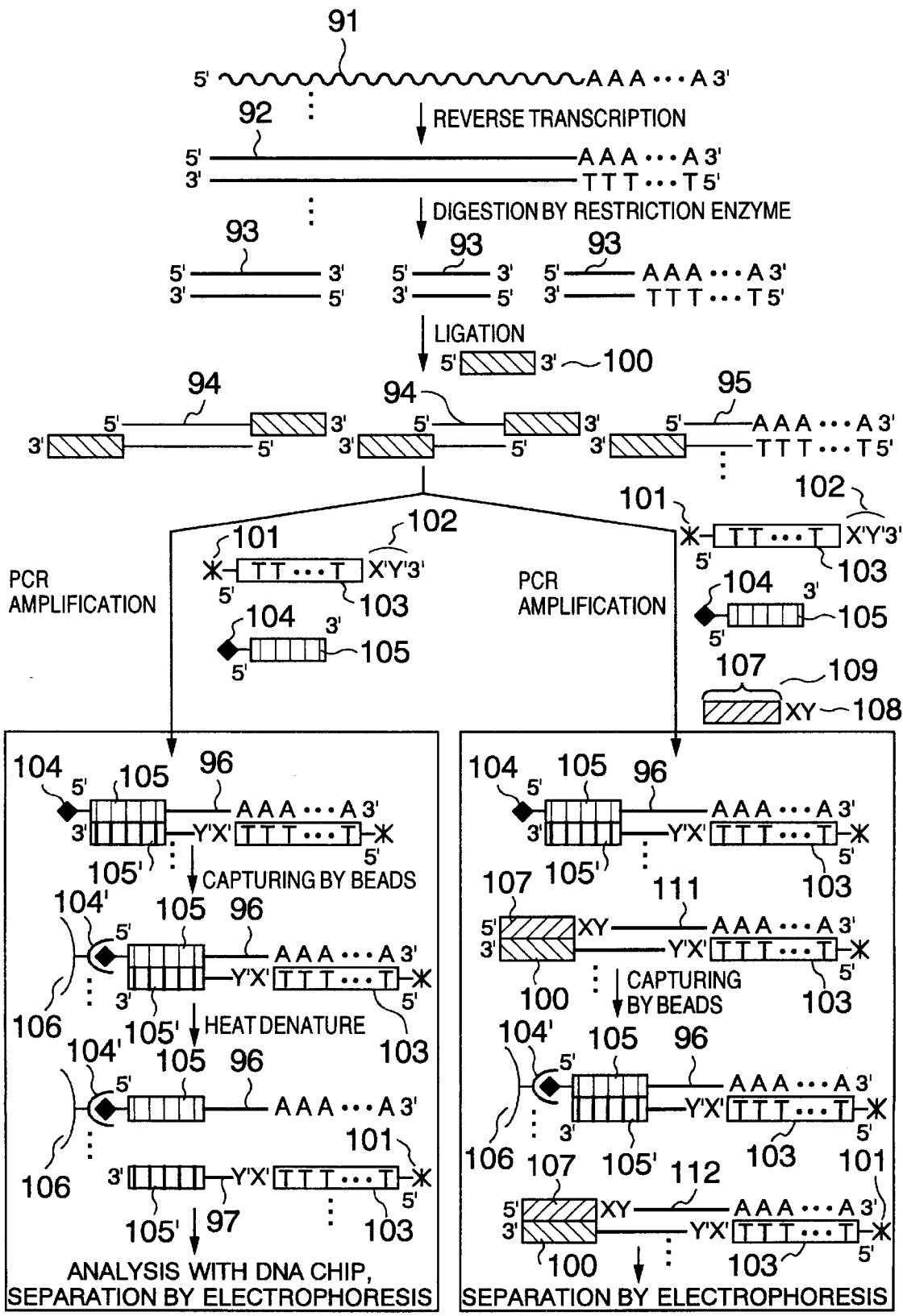
FIG. 7 shows a sample preparation process in Embodiment 3.

The present invention can be used to take out the fragments originated in the unknown genes by replacing the fluorophore label with biotin. The sample preparation process in this embodiment is shown in FIG. 7.

Double stranded cDNAs 92 are produced by reverse transcription from mRNA 91. They are digested by a restriction enzyme to obtain DNA fragments 93. Oligomers 100 having a known sequence at least one terminus are produced through similar processes to that in Embodiments 1 and 2. Each of the produced fragments (numeral 94) has the oligomer sequence 100 at the both termini, or each of the produced fragments (numeral 95) has both of the oligomer and polyA sequences at the termini. The two types of the sample preparation methods can be used here.

In the first method, the primer I (numeral 103) (primer of pair of primers) of the primer set I has the oligo T sequence at 5' end together with 2 base selective sequences X'Y' (X' represents either of A, G, or C and Y' represents either of A, T, G or C) (numeral 102) at 3' end and labeled with fluorophore (*) 101 at 5' end. The primer III (numeral 105) (specific primer) having a known sequence, which hybridizes with the target, is labeled with biotin (♦) 104 instead of fluorophore. In FIG. 7, numeral 105' denotes a base sequence complementary to the base sequence of primer III.

The PCR reactions are carried out with these two primers I and III and fragments 94 and 95 as template DNAs. This process amplifies the DNA fragments originated in known genes. The products are purified by a molecular sieving column and the unreacted primers are removed from the products.

The PCR products 96 by the primers I and III. That is, biotin-labeled products are trapped on the surface of bead 106 having streptavidin 104'. The fluorophore-labeled strands 97 can be easily detached from the complementary strands trapped on the surface of the beads, by heating, an alkaline treatment or the like.

The fluorophore-labeled strands are analyzed with a DNA chip or gel electrophoresis. The abundance of the known genes in a cell or tissue (gene expression profiling) is obtained from the analysis. Of course, all possible primer I and III pairs are analyzed independently. In this embodiment, the gene expression profiling or known genes is extracted.

For obtaining the gene expression of unknown genes, as a second method, the following sample preparation process is used. The reactions are carried out by the same way as above mentioned with the same primers. In the second method, the primer II (numeral 109) (primer of pair of primers) of the primer set II, the primer I of the primer set I and primer III of the primer set III are used in the PCR. The primer II has selective sequence XY (X and Y represents either of A, T, G or C) 108 at 3' end. Base sequence 107 is complementary to the oligomer sequence 100. As a result of PCR, the fragments 96 are generated by the primer I and III, the fragments 111 are generated by the primer I and II.

However, this time, the fragments 96 trapped on the beads 106 are removed and the residual components (the fragments 112) in a solution are used for the analysis. The residual components in the solution include fragments related to the unknown genes. Therefore, the electropherograms of the fragments (numeral 112) from the unknown genes are obtained.

Of course, the fragments from the unknown genes can be sequenced after fractionating DNA bands followed by PCR amplification. A useful instrument for the fragment fractionation or sorting has been already proposed in Japanese Patent Application Laid-Open No. 181164/1995. These DNA bands can be obtained by cutting out the corresponding DNA bands in a slab gel electrophoresis.

The combination of the fragment sorter and the present invention create a new valuable application in DNA analysis. Target genes or new genes can be extracted automatically. With the progress of the human genome project, the gene function analysis becomes increasingly important. The gene expression profiling is obtained by getting the population or the abundance of mRNA in a cell or a tissue. The abundance of the mRNA changes with the environment. Unknown genes can be selectively detected with the present invention as mentioned above.

The only fragments originated in the unknown genes can be labeled with a fluorophore and emit fluorescence by laser irradiation. One of the example of the fragment sorting instrument is the gel electrophoresis system which has a plurality of capillaries and in which a sheath flow is formed at each end of capillaries.

The instrument consists of an electrophoresis part, a data acquisition system, and a monitor. The gel electrophoresis system is an automated fluorescent DNA analyzer with a capillary gel array as a DNA separator. DNAs are separated in the gel and eluted from the ends of the capillaries into the buffer solution where the sheath flow carries the DNA bands to the laser irradiated region without the DNA band diffusion. The fluorescence signal is detected with the detector and the signal is used to move a sampling tray if necessary. The sampling signal is transferred to the sampling tray controller when the signal intensity is over a determined value.

When unknown and differentially expressed genes are the target, the standard sample and the sample including the target have to be labeled with different fluorophores from each other. As the selective fluorophore labeling of the unknown gene fragments are already mentioned in Embodiments 1–3, it is not necessary to repeat the process. The difference of the two different fluorescence signals from the two samples is monitored with the color selective detector and when the difference is over the threshold, the DNA bands are automatically fractionated in the sampling tray.

EMBODIMENT 4

Figure 8:
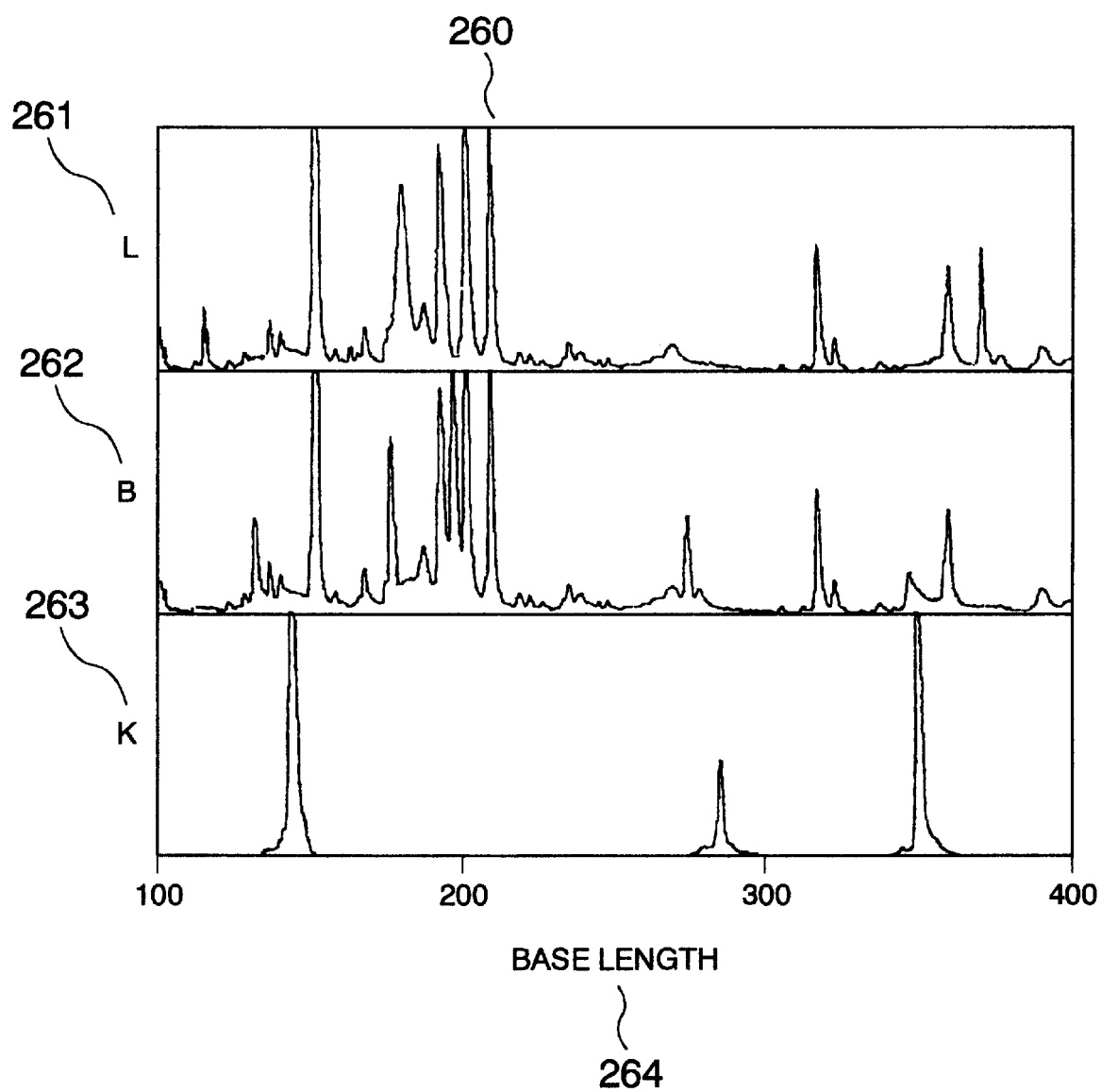
FIG. 8 shows a part of the electropherograms obtained with human liver tissue cell as well as brain cell, in Embodiment 4.

A part of the electropherograms 260 obtained with human liver tissue cells as well as brain cells are shown in FIG. 8. In FIG. 8, numeral 264 denotes a base length, and the vertical axis represents the relative fluorescent intensity.

mRNAs from human liver tissue cells and human brain cells are extracted based on the guanidinium thiocyanate method (Molecular Cloning (1989), 7.19–7.22 (Extraction of RNA with Guanidinium Thiocyanate Followed by Centrifugation in Cesium Chloride Solutions)). cDNAs are prepared based on Gubler and Hoffman method (Molecular Cloning (1989), 8.15–8.20 (Replacements Synthesis of the Second Strand of cDNA, Primed Synthesis of the Strand of cDNA)), using oligo dT primers.

cDNAs prepared above mentioned are digested with restriction enzyme Mbo I to obtain cDNA fragments, and oligomers having known base sequence are ligated to the digested DNA fragments by restriction enzyme Mbo I. The cDNA fragments originated in the liver tissue cell and the cDNA fragments originated in the brain cell are, respectively, ligated with different oligomers each having a different known base sequence.

In PCR, the primer labeled with FITC (fluoreceine isothiocyanate) for amplifying a number of cDNA fragments originated in the liver tissue cell, and the the primer labeled with Texas Red (sulforhodamine 101 acid chloride) for amplifying a number of cDNA fragments originated in the brain cell, and the the primer labeled with fluorophore different from FITC and Texas Red for amplifying a number of DNA fragments originated in known genes (for example, insuline, β-actin) are used.

The electropherogram 261 is originated in the signals by the genes expressing in liver tissue cells, the electropherogram 262 is originated in the signals by the genes expressed in brain tissue cells, and the electropherogram 263 is originated in the signals known genes.

The fluorophores FITC and Texas Red are used for labeling the primers used in PCR. Of course, other fluorophores such as JOE, FAM, TAMRA and ROX from Perkin Elmer ABD can be used as well.

A DNA fragment analysis method and a reagent kit for use in the DNA fragment analysis method in this invention include methods and kits which are described as follows:

(a1) A DNA fragment analysis method comprising:
   i) amplifying a number of copy of at least one DNA fragment in a DNA fragment mixture by PCR, using a pair of primers (that is, a pair of common primers) which can amplify a number of copy of a DNA fragment in the DNA fragment mixture and a specific primer which has a base sequence complementary to a part of a known base sequence of the at least one DNA fragment (the specific primer hybridizes specifically with a base sequence of the DNA fragment at a position between a priming site of one of primer the pair of primers and a priming site of another primer of the pair of primers); and
   ii) separating, by electrophoresis, DNA fragments produced in step i).

(a2) A DNA fragment analysis method according to (a1), wherein at least one primer in the pair of primers and the specific primer is labeled with a fluorophore.

(a3) A DNA fragment analysis method according to (a1), wherein a label labeling the specific primer is different from a label labeling the pair of primers.

(a4) A DNA fragment analysis method according to (a1), wherein a label labeling the specific primer is different from a label labeling the pair of primers, and the label labeling the specific primer is a fluorophore.

(a5) A DNA fragment analysis method according to (a1), wherein a label labeling the specific primer is different from a label labeling the pair of primers, and the label labeling the specific primer is biotin.

(a6) A DNA fragment analysis method according to (a1), wherein an oligonucleotide having a known base sequence is connected to at least one end of a DNA fragment in the DNA fragment mixture, and one primer of the pair of primers has a base sequence complementary to a base sequence of the oligonucleotide.

(a7) A DNA fragment analysis method according to (a1), wherein an oligonucleotide having a known base sequence is connected to at least one end of a DNA fragment in the DNA fragment mixture by a ligation reaction, and one primer of the pair of primers has a base sequence complementary to a base sequence of the oligonucleotide.

(a8) A DNA fragment analysis method according to (a1), wherein an oligonucleotide having a base sequence of a polyA sequence is connected, by polyA tailing reaction, to at least one end of a DNA fragment in the DNA fragment mixture, and one primer of the pair of primers has a base sequence complementary to a base sequence of the oligonucleotide having the polyA sequence.

(a9) A DNA fragment analysis method according to (a1), wherein an oligonucleotide having a known base sequence is connected to at least one end of a DNA fragment in the DNA fragment mixture, and at least one primer of the pair of primers has a base sequence complementary to a base sequence of the oligonucleotide and a selective sequence having arbitrary bases composed of 1 base to 4 bases selected from the group consisting of A, T, G and C, at 3' end of the one primer of the pair of primers, the selective sequence discriminates base species of 1 base to 4 bases at 5' end of a DNA fragment in the DNA fragment mixture.

(a10) A DNA fragment analysis method according to (a1), wherein an oligonucleotide having a known base sequence is connected to at least one end of a DNA fragment in the DNA fragment mixture, at least and one primer of the pair of primers has a base sequence complementary to a base sequence of the oligonucleotide and a selective sequence having arbitrary bases composed of 1 base to 4 bases selected from the group consisting of A, T, G, and C at 3' end of the one primer of the pair of primers, the selective sequence discriminates base species of 1 base to 4 bases at 5' end of a DNA fragment in the DNA fragment mixture, and the selective sequence is directly adjacent to 3' end of a base sequence complementary to a base sequence of the oligonucleotide, a part of base in the base sequence complementary to the base sequence of the oligonucleotide is replaced by a nucleotide analogue or base species mismatching with the base sequence of the oligonucleotide.

(a11) A DNA fragment analysis method according to (a1), wherein, in step i), fluorescence generated from a fluorophore labeling the DNA fragments produced in step i) is detected.

(a12) A DNA fragment analysis method according to (a1), wherein a plurality pairs of the pair of primers are use in step i), one primer each of the plurality pairs of the pair of primers is selected from a first primer set and another primer each of the plurality pairs of the pair of primers is selected from a second primer set, and each set of the first and the second primer sets comprises primers each having a base sequence composed of a combination of 1 base or 2 bases selected from the group consisting of A, T, G and C at 3' end.

(a13) A DNA fragment analysis method comprising:
   i) amplifying a number of copy of a plurality of DNA fragments in a DNA fragment mixture by PCR, using at least a pair of primers (that is, a pair of common primers) which can amplify a number of copy of a DNA fragment in the DNA fragment mixture;
   ii) amplifying a number of copy of a plurality of DNA fragments produced in step i), using the pair of primers and a specific primer which has a base sequence complementary to a part of a known base sequence of the DNA fragments produced in step i) (the specific primer hybridizes specifically with a base sequence of the DNA fragment at a position between a priming site of one of primer the pair of primers and a priming site of another primer of the pair of primers); and iii) separating, by electrophoresis, DNA fragments produced in step ii).

(a14) A reagent kit used in a DNA fragment analysis method according to (a1) comprising:

a pair of primers (that is, a pair of common primers) which can amplify a number of copy of a DNA fragment in a DNA fragment mixture; and a specific primer which has a base sequence complementary to a part of a known base sequence of at least one DNA fragment in the DNA fragment mixture (the specific primer hybridizes specifically with a base sequence of the DNA fragment at a position between a priming site of one of primer the pair of primers and a priming site of another primer of the pair of primers).

(b1) A DNA fragment analysis method comprising:

i) amplifying a number of copy of a plurality of DNA fragments in a DNA fragment mixture by PCR, using a first primer and a second primer as primers, wherein the first primer and the second primer can amplify a number of copy of the plurality of DNA fragments in the DNA fragments mixture, and the third primer has a base sequence complementary to a part of a known base sequence of DNA fragments amplified by using the first primer and the second primer (the specific primer hybridizes specifically with a base sequence of the DNA fragment at a position between a priming site of the first primer and a priming site of the second primer); and ii) separating, by electrophoresis, DNA fragments produced in step i).

(b2) A DNA fragment analysis method according to (b1), wherein the number of copy of the plurality of DNA fragments in the DNA fragment mixture is amplified by the third primer and one primer of the first primer and the second primer.

(b3) A DNA fragment analysis method according to (b1), wherein base lengths of a plurality of DNA fragments in the DNA fragment mixture amplified by the third primer and one primer of the first primer and the second primer are less than base lengths of a plurality of DNA fragments in the DNA fragment mixture amplified by the first primer and the second primer.

(b4) A DNA fragment analysis method according to (b1), wherein any one of the first primer, the second primer and the third primer is labeled with a fluorophore.

(b5) A DNA fragment analysis method according to (b1), wherein any two of the first primer, the second primer and the third primer are labeled with a different fluorophore from one another.

(b6) A DNA fragment analysis method according to (b1), wherein the first primer, the second primer and the third primer are labeled with a different fluorophore from one another.

(b7) A reagent kit used in a DNA fragment analysis method according to (b1) comprising:

a first primer and a second primer which can amplify a number of copy of a plurality of DNA fragments in a DNA fragment mixture; and a third primer which has a base sequence complementary to a part of a known base sequence of the plurality of DNA fragments amplified by using the first primer and the second primer.

(c1) A DNA fragment analysis method comprising:

i) preparing a plurality of double stranded DNA fragments having a first oligonucleotide with known base sequence at one 3' end of the double stranded DNA fragments and having a second oligonucleotide with known base sequence at another 3' end of the double stranded DNA fragments;

ii) amplifying a number of copy of a plurality of double stranded DNA fragments in a DNA fragment mixture by PCR, using as templates the plurality of the double stranded DNA fragments in the DNA fragment mixture, and using a first primer, a second primer and a third primer as primers, wherein the a first primer has a base sequence complementary to a base sequence of the first oligonucleotide, and wherein the second primer has a base sequence complementary to a base sequence of the second oligonucleotide, and wherein the third primer has a base sequence complementary to a part of base sequence between a base sequence being at 5' end of one strand of a double stranded DNA fragment and being complementary to a base sequence of the second oligonucleotide and the first oligonucleotide at 3' end of the one strand of a double stranded DNA fragment which can be amplified by the first primer and the second primer; and iii) separating, by electrophoresis, DNA fragments produced in step ii).

(c2) A DNA fragment analysis method according to (c1), wherein the number of copy of the plurality of DNA fragments in the DNA fragment mixture is amplified by the third primer and one primer of the first primer and the second primer.

(c3) A DNA fragment analysis method according to (c1), wherein base lengths of the plurality of DNA fragments in the DNA fragment mixture amplified by the third primer and one primer of the first primer and the second primer less than base lengths of the plurality of DNA fragments in the DNA fragment mixture amplified by the first primer and the second primer.

(c4) A DNA fragment analysis method according to (c1), wherein primers specifically hybridizing with DNA fragments originated in different genes and each being labeled with a different fluorophore are used as the third primer.

(c5) A DNA fragment analysis method according to (c1), wherein step ii) comprising:

a) amplifying a number of copy of the plurality of the double stranded DNA fragments in the DNA fragment mixture by PCR using as templates the plurality of the double stranded DNA fragments in the DNA fragment mixture, and using the first primer and the second primer as primers; and b) amplifying a number of copy of double stranded DNA fragments generated in step a) using the first primer, the second primer and the third primer.

(c6) A DNA fragment analysis method according to (c1), wherein any one of the first primer, the second primer and the third primer is labeled with a fluorophore.

(c7) A DNA fragment analysis method according to (c1), wherein any two of the first primer, the second primer and the third primer are labeled with a different fluorophore from one another.

(c8) A DNA fragment analysis method according to (c1), wherein a fluorophore labeling the first primer is different from a fluorophore labeling the second primer.

(c9) A DNA fragment analysis method according to (c1), wherein the first primer, the second primer and the third primer are labeled with a different fluorophore from one another.

(c10) A DNA fragment analysis method according to (c1), wherein at least one of the first primer and the second primer has a selective sequence having a arbitrary base composed of 1 base to 4 bases selected from the group consisting of A, T, G and C at 3' end thereof, and the selective sequence discriminates base species of 1 base to 4 bases at 5' end of the DNA fragment in the DNA fragment mixture.

(c11) A DNA fragment analysis method according to (c1), wherein the second primer has a selective sequence having a arbitrary base composed of 1 base to 4 bases selected from the group consisting of A, T, G and C, at 3' end of a base sequence complementary to the base sequence of the second oligonucleotide, the selective sequence discriminates base species of 1 base to 4 bases at 5' end of the DNA fragment in the DNA fragment mixture, and a part of base in the base sequence complementary to the base sequence of the second oligonucleotide is replaced by a nucleotide analogue or base species mismatching with the base sequence of the oligonucleotide.

(c12) A DNA fragment analysis method according to (c1), wherein the first primer has a selective sequence having a arbitrary base composed of 1 base to 4 bases selected from the group consisting of A, T, G and C, at 3' end of a base sequence complementary to the base sequence of the first oligonucleotide, the selective sequence discriminates base species of 1 base to 4 bases at 5' end of the DNA fragment in the DNA fragment mixture, and a part of base in the base sequence complementary to the base sequence of the first oligonucleotide is replaced by a nucleotide analogue or base species mismatching with the base sequence of the oligonucleotide.

(c13) A DNA fragment analysis method according to (c1), wherein a base sequence of the first oligonucleotide is a base sequence of any one of a polyA sequence, a polyT sequence, a polyG sequence and a polyc sequence.

(d1) A DNA fragment analysis method comprising:
  i) hybridizing an oligomer having a base sequence of a polyT sequence with a polyA sequence at 3' end of each of a plurality of mRNAs;
  ii) preparing a double stranded cDNA by complementary strand synthesis using the plurality of mRNAs as templates, and using the oligomer as a primer;
  iii) digesting the double stranded cDNA with a restriction enzyme to obtain a plurality of double stranded cDNA fragments,
  wherein one strand of each of the plurality of double stranded CDNA fragments has a polyT sequence at 5' end;
  iv) connecting an oligonucleotide having known base sequence to 3' end of the one strand of each of the plurality of double stranded cDNA fragments;
  v) performing PCR using as a template a complementary strand with a DNA strand having a base sequence of the oligonucleotide at 3' end and having a base sequence of a polyT sequence at 5' end, and using a first primer, a second primer and a third primer as primers,
  wherein the first primer has a base sequence of a polyT sequence labeled with a fluorophore at 5' end and has at 3' end a first selective sequence composed of two bases selected from the group consisting of A, T, G and C, and the first selective sequence discriminates two base species directly adjacent to 5' end of a base sequence of a polyA sequence at 3' of another strand of each of the plurality of double stranded cDNA fragments,
  wherein the second primer has a second selective sequence composed of two bases selected from the group consisting of A, T, G and C, at 3' end of a base sequence complementary with the oligonucleotide, and the second selective sequence discriminates two base species directly adjacent to 5' end of a base sequence of the oligonucleotide of the one strand of each of the plurality of double stranded cDNA fragments,
  and wherein the third primer has a base sequence complementary to a part of a base sequence between a polyA sequence at 3' end of the template and 3' end of the second selective sequence at side of 5' end of the template which can be amplified by the first primer and the second primer; and
  vi) separating, by electrophoresis, DNA fragments produced in step v). (d1) is based on FIG. 1.

(d2) A DNA fragment analysis method comprising:
  i) hybridizing an oligomer having a base sequence of a polyT sequence with a polyA sequence at 3' end of each of a plurality of mRNAs;
  ii) preparing a double stranded cDNA by complementary strand synthesis using the plurality of mRNAs as templates, and using the oligomer as a primer;
  iii) digesting the double stranded cDNA with a class IIS restriction enzyme to obtain a solution contain a plurality of double stranded cDNA fragments,
  wherein one strand of each of the plurality of double stranded cDNA fragments has a cohesive end composed of 4 bases at 5' end and has a base sequence of a polyA sequence at 3' end;
  iv) dividing the solution into 64 vessels, and adding separately each species of 64 oligonucleotide species into the 64 vessels for connecting the oligonucleotide species to the cohesive end of each of the plurality of double stranded cDNAs,
  wherein each of base sequences of 64 oligonucleotide species is composed of any one of base sequences each having a base sequence part consisting of all possible combinations of 3 bases selected from the group consisting A, T, G and C, directly adjacent to 5' end of any one of a first, a second, a third and a fourth oligomers each having A, T, G and C directly adjacent to 5' end of a base sequence of the oligomer;
  v) amplifying a number of copy of a DNA fragment in a solution in each of vessels by PCR, using as a template a complementary strand of a DNA strand having a base sequence of the oligomer at 3' end and a base sequence of a polyT sequence at 5' end, and using a first primer, a second primer and a third primer as primers,
  wherein the first primer has a selective sequence composed of two bases selected from the group consisting of A, T, G and C, at 3' end of a base sequence of a polyT sequence which is labeled at 5' end by a first fluorophore, the selective sequence discriminates two base species directly adjacent to 5' end of a base sequence of a polyA sequence at 3' of the one strand of each of the plurality of double stranded cDNA fragments,
  wherein the second primer has a base sequence complementary to the oligonucleotide species, and wherein the third primer has a base sequence complementary to a part of base sequence between 5' end of base sequence of a polyA sequence at 3' end of the template and 3' end of a base sequence of the cohesive end at side of 5' end of the template which can be amplified by the first primer and the second primer, and the third primer has a second fluorophore at 5' end; and vi) separating, by electrophoresis, DNA fragments produced in each of vessels in step v). (d2) is based on FIG. 6.

(d3) A DNA fragment analysis method comprising:

i) hybridizing an oligomer having a base sequence of a polyT sequence with a polyA sequence at 3' end of each of a plurality of mRNAs;

ii) preparing a double stranded cDNA by complementary strand synthesis using the plurality of mRNAs as templates, and using the oligomer as a primer;

iii) digesting the double stranded cDNAs with a restriction enzyme to obtain a plurality of double stranded cDNA fragments having a polyT sequence at 5' end of one strand of each of the double stranded cDNAs;

iv) connecting an oligonucleotide having a known base sequence to 3' end of the one strand of each of the double stranded cDNAs;

v) amplifying a number of copy of a DNA fragment by PCR using as a template a complementary strand of DNA strand having a base sequence having a base sequence of the oligomer at 3' end and a base sequence of a polyT sequence at 5' end, and using a first primer and a second primer as primers, wherein the first primer has a selective sequence composed of two bases selected from the group consisting of A, T, G and C, at 3' end of a base sequence of a polyT sequence which is labeled at 5' end by a fluorophore, the selective sequence discriminates two base species directly adjacent to 5' end of a base sequence of a polyA sequence at 3' of another strand of each of the plurality of double stranded cDNA fragments, and wherein the second primer has a base sequence complementary to a part of base sequence between 5' end a base sequence of a polyA sequence at 3' end of the template and 3' end of a base sequence complementary to a base sequence of the oligonucleotide at side of 5' end of the template which can be amplified by the first primer, the second primer is labeled with biotin at 5' end;

vi) capturing, by a biotin-avidin binding, double stranded DNA fragments amplified by the first primer and the second primer in step v), on a solid support;

vii) denaturing the double stranded DNA fragments captured on the solid support, by a thermal denaturing; and viii) separating, by electrophoresis, single stranded DNA fragments produced by the thermal treatment in step vii). (d3) is based on process of a left side in FIG. 7.

(d4) A DNA fragment analysis method comprising:

i) hybridizing an oligomer having a base sequence of a polyT sequence with a polyA sequence at 3' end of each of a plurality of mRNAs;

ii) preparing a double stranded cDNA by complementary strand synthesis using the plurality of mRNAs as templates, and using the oligomer as a primer;

iii) digesting the double stranded cDNAs with a restriction enzyme to obtain a plurality of double stranded cDNA fragments having a polyT sequence at 5' end of one strand of each of the double stranded cDNAs;

iv) connecting an oligonucleotide having a known base sequence to 3' end of the one strand of each of the double stranded cDNAs;

v) amplifying a number of copy of a DNA fragment by PCR using as a template a complementary strand of DNA strand having a base sequence having a base sequence of the oligomer at 3' end and a base sequence of a polyT sequence at 5' end, and using a first primer, a second primer and a third primer as primers, wherein the first primer has a first selective sequence composed of two bases selected from the group consisting of A, T, G and C, at 3' end of a base sequence of a polyT sequence which is labeled at 5' end by a first fluorophore, the first selective sequence discriminates two base species directly adjacent to 5' end of a base sequence of a polyA sequence at 3' of another strand of each of the plurality of double stranded cDNA fragments, wherein the second primer has a second selective sequence composed of two bases selected from the group consisting of A, T, G and C, at 3' end of a base sequence complementary to the oligonucleotide, the second selective sequence discriminates two base species directly adjacent to 5' end of a base sequence of the oligonucleotide of the one strand of each of the plurality of double stranded cDNA fragments, and wherein the third primer has a base sequence complementary to a part of a base sequence between a polyA sequence at 3' end of the template and 3' end of the second selective sequence at side of 5' end of the template which can be amplified by the first primer and the second primer, and the third primer is labeled with biotin at 5' end;

vi) capturing, by a biotin-avidin binding, double stranded DNA fragments amplified by the first primer and the third primer in step v), on a solid support;

vii) separating, by electrophoresis, DNA fragments amplified by the first primer and the second primer in step v). (d4) is based on process of a right side in FIG. 7.

(d5) A DNA fragment analysis method comprising:

i) hybridizing an oligomer having a base sequence of a polyT sequence with a polyA sequence at 3' end of each of a plurality of mRNAs;

ii) preparing a double stranded cDNA by complementary strand synthesis using the plurality of mRNAs as templates, and using the oligomer as a primer;

iii) digesting the double stranded cDNAs with a restriction enzyme to obtain a plurality of double stranded cDNA fragments having a polyT sequence at 5' end of one strand of each of the double stranded cDNAs;

iv) connecting an oligonucleotide having a known base sequence to 3' end of the one strand of each of the double stranded cDNAs;

v) amplifying a number of copy of a DNA fragment by PCR using as a template a complementary strand of DNA strand having a base sequence of the oligomer at 3' end and a base sequence of a polyT sequence at 5' end, and using a first primer and a second primer as primers, wherein the first primer has a first selective sequence composed of two bases selected from the group consisting of A, T, G and C, at 3' end of a base sequence of a polyT sequence which is labeled at 5' end by a first fluorophore, the first selective sequence discriminates two base species directly adjacent to 5' end of a base sequence of a polyA sequence at 3' of another strand of each of the plurality of double stranded cDNA fragments, and wherein the second primer has a second selective sequence composed of two bases selected from the group consisting of A, T, G and C, at 3' end of a base sequence complementary to the oligonucleotide, the second selective sequence discriminates two base species directly adjacent to 5' end of a base sequence of the oligonucleotide of the one strand of each of the plurality of double stranded cDNA fragments;

vi) amplifying a number of a copy of DNA fragment by PCR using as a new template a complementary strand of a DNA strand produced in step v), and using the first, the second and a third primer as primers, wherein the third primer has a base sequence complementary to a part of a base sequence between a polyA sequence at 3' end of the new template and 3' end of the second selective sequence at side of 5' end of the new template which can be amplified by the first primer and the second primer; and vii) separating, by electrophoresis, DNA fragments produced in step vi).

(d6) A DNA fragment analysis method comprising:

i) hybridizing an oligomer having a base sequence of a polyT sequence with a polyA sequence at 3' end of each of a plurality of mRNAs;

ii) preparing a double stranded cDNA by complementary strand synthesis using the plurality of mRNAs as templates, and using the oligomer as a primer;

iii) digesting the double stranded cDNAs with a restriction enzyme to obtain a plurality of double stranded cDNA fragments having a polyT sequence at 5' end of one strand of each of the double stranded cDNAs;

iv) connecting an oligonucleotide having a known base sequence to 3' end of the one strand of each of the double stranded cDNAs;

v) amplifying a number of copy of a DNA fragment by PCR using as a template a complementary strand of DNA strand having a base sequence having a base sequence of the oligomer at 3' end and a base sequence of a polyT sequence at 5' end, and using a first primer, a second primer and a third primer as primers, wherein the first primer has a first selective sequence composed of two bases selected from the group consisting of A, T, G and C, at 3' end of a base sequence of a polyT sequence, the first selective sequence discriminates two base species directly adjacent to 5' end of a base sequence of a polyA sequence at 3' of another strand of each of the plurality of double stranded cDNA fragments, wherein the second primer is labeled at 5' end by a first fluorophore, and the second primer has a second selective sequence composed of two bases selected from the group consisting of A, T, G and C, at 3' end of a base sequence complementary to the oligonucleotide, the second selective sequence discriminates two base species directly adjacent to 5' end of a base sequence of the oligonucleotide of the one strand of each of the plurality of double stranded cDNA fragments, and wherein the third primer has a base sequence complementary to a part of a base sequence between a polyA sequence at 3' end of the template and 3' end of the second selective sequence at side of 5' end of the template which can be amplified by the first primer and the second primer, and the third primer is labeled at 5' end by a second fluorophore; and vi) separating, by electrophoresis, DNA fragments produced in step v).

In the above drawings, numerals 1, 61 and 91 denote a sample mRNA; numerals 2, 62 and 92 denote a double stranded cDNA; numeral 4 denotes a CDNA fragment lying between polyT sequence and oligomer 12; numeral 5 denotes cDNA fragments excepting CDNA 4 fragments; numerals 6, 7, 6*a*' 6*b*, 6*c*, 6*d*, 7*a*, 80, 81 and 111 denotes a PCR amplification product labeled with fluorophore; numeral 9 denotes a polyA sequence; numeral 10 denotes an oligomer having polyT sequence; numeral 11 denotes a titerplate; numerals 12, 70 and 100 denote an oligomer having known sequence; numerals 14, 16, 22, 75, 102 and 108 denote a selective sequence; numerals 17, 18, 76, 78 and 101 denote a fluorophore; numerals 19, 77 and 105 denote a specific primer; numerals 19', 77' and 105' denote a base sequence complementary to a specific primer; numeral 20 denotes a primer; numerals 13, 15, 74, 103 and 109 denote a primer in a primer set; numeral 21 denotes a complementary sequence to oligomer 23; numeral 23 denotes an oligomer connected to the end of DNA fragment 24; numerals 24, 24' and 93 denote a DNA fragment; numeral 25 denotes a base forming mismatch base pairing; numeral 30 denotes a case of hybridization of primer 20 and DNA fragment 24 connected with oligomer 23 at one end without mismatch base pairing; numeral 31 denotes a case of hybridization of primer 20 and DNA fragment 24' connected with oligomer 23 at one end with mismatch base pairing; numeral 32 denotes a case of preventing sensitively occurrence of complementary strand synthesis with mismatch base pairing at one end; numeral 40 denotes a relative fluorescent intensity; numerals 1, 52 and 264 denote a base length; 42 denotes lane (a); numeral 43 denotes lane (b); numeral 44 denotes lane (c); numerals 50 and 260 denote a part of obtained electropherograms; numeral 51 denotes a combination of selective sequence of primers used in PCR; numeral 63 denotes a double stranded DNA fragment; numeral 64 denotes an end part of single stranded DNA; numeral 65 denotes a DNA fragment connected with oligomer 70 having a known sequence at one end; numeral 66 denotes a DNA fragment connected with oligomers 70 having a known sequence at both ends; numeral 67 denotes a DNA fragment connected with oligomer 70 having a known sequence at one end and connected with polyA sequence at another end; numeral 71 denotes a part of common sequence; numeral 72 denotes a part of arbitrary sequence; numeral 73 denotes a primer having a sequence complementary to a part of common sequence 71; numeral 94 denotes a DNA fragment connected with oligomer 100 having a known sequence at one end; 95 denotes a DNA fragment connected with oligomer 100 having a known sequence at one end and connected with a polyA sequence at another end; numeral 96 denotes a PCR amplification product; numeral 97 denotes a DNA strand labeled with a fluorophore; numeral 104 denotes biotin; numeral 106 denotes beads tagged with streptavidin; numeral 107 denotes a sequence complementary to oligomer 100; numeral 112 denotes a group of unknown DNA fragments; numeral 261 denotes an electropherogram showing signals from expressed genes in liver; numeral 262 denotes an electropherogram showing signals from expressed genes in brain; and numeral 263 denotes an electropherogram showing signals from known genes.

What is claimed is:

1. A DNA fragment preparation method for gene expression profiling, comprising the steps of:
   i) preparing a plurality of DNA fragments including a sequence-known DNA fragment and a sequence-unknown DNA fragment from a sample DNA; and
   ii) amplifying fragments each having a shorter length than the length of the sequence-known DNA fragment and the sequence-unknown DNA fragment by polymerase chain reaction (PCR), using the DNA fragments as templates and using first and second primers, each of which hybridizes with a terminus sequence of each of the DNA fragments, and a specific primer which hybridizes specifically with a base sequence of the sequence-known DNA fragment at a position between a priming site of the first primer and a priming site of the second primer,
   wherein, by using the first primer, the second primer and the specific primer at the same time, and by competitive reactions occurring between PCR by the first primer and the second primer and PCR by the second primer and the specific primer, the fragments each having a part of the base sequence of the sequence-known DNA fragment and having a shorter length than the lengths of the PCR products by the first primer and the second primer are produced as major products in the PCR by the second primer and the specific primer.

2. A DNA preparation method according to claim 1, wherein the first primer or the second primer is labeled with a fluorophore and the specific primer is labeled with another fluorophore different from the fluorophore labeling the first primer or the second primer.

3. A DNA preparation method according to claim 1, wherein the first primer is labeled with a fluorophore and the specific primer is labeled with another fluorophore different from said fluorophore labeling the first primer.

4. A DNA preparation method according to claim 1, wherein the specific primer is only labeled with a fluorophore.

5. A DNA preparation method according to claim 1, wherein the first primer is only labeled with a fluorophore.

6. A DNA fragment preparation method for gene expression profiling comprising the steps of:
   i) preparing a plurality of double stranded DNA fragments including a sequence-known DNA fragment and a sequence-unknown DNA fragment from a sample DNA;
   ii) ligating an oligomer having a known base sequence to one 3'-terminus of the double stranded DNA fragments by a ligation reaction to obtain a ligated sequence-known DNA fragment and a ligated sequence-known DNA fragment; and
   iii) by a polymerase chain reaction (PCR), amplifying double stranded fragments each having a shorter length than the length of the ligated sequence-known DNA fragment and the ligated sequence-unknown DNA fragment, using the ligated sequence-known DNA fragment and the ligated sequence-unknown DNA fragment as templates and using a first primer which hybridizes with a base sequence at the 3'-terminus of one strand, being not ligated to the oligomer, of the ligated sequence-known DNA fragment and the ligated sequence-unknown DNA fragment, a second primer which hybridizes with the known base sequence of the oligomer of the ligated sequence-known DNA fragment and the ligated sequence-unknown DNA fragment, and a specific primer that hybridizes specifically with a base sequence complementary with one strand, being ligated to the oligomer, of the ligated sequence-known DNA fragment, at a position between a base sequence complementary with the first primer and a base sequence complementary with the second primer,
   wherein, by using the first primer, the second primer, and the specific primer at the same time, and by competitive reactions occurring between PCR by the first primer and the second primer and PCR by the second primer and the specific primer, the double stranded fragments each having a part of the base sequence of the sequence-known DNA fragment and having a shorter length than lengths of PCR products by the first primer and the second primer are produced as major products in the PCR by the second primer and the specific primer.

7. A DNA preparation method according to claim 6, wherein the first primer or the second primer is labeled with a fluorophore and the specific primer is labeled with another fluorophore different from the fluorophore labeling the first primer or the second primer.

8. A DNA preparation method according to claim 6, wherein the first primer is labeled with a fluorophore and the specific primer is labeled with another fluorophore different from the fluorophore labeling the first primer.

9. A DNA preparation method according to claim 6, wherein the specific primer is only labeled with a fluorophore.

10. A DNA preparation method according to claim 6, wherein the first primer is only labeled with a fluorophore.

11. A DNA fragment preparation method for gene expression profiling comprising the steps of:
   i) preparing a plurality of double stranded cDNA fragments including a sequence-known cDNA fragment and a sequence-unknown cDNA fragment from sample mRNAs, the double stranded cDNA fragments each consisting of a first single strand having a poly A sequence at the 3' terminus and a second single strand having a poly T sequence at the 5' terminus;
   ii) ligating an oligomer having a known base sequence to the 3'-terminus of the second single strand of the double stranded cDNA fragments by a ligation reaction to obtain a ligated sequence-known cDNA fragment and a ligated sequence-unknown cDNA fragment; and
   iii) by polymerase chain reaction (PCR), amplifying double stranded fragments each having a shorter length than the length of the ligated sequence-known cDNA fragment and the ligated sequence-unknown cDNA fragment, using the ligated sequence-known cDNA fragment and the ligated sequence-unknown cDNA as templates and using a first primer which hybridizes with the poly A sequence at the 3' terminus of the first single strand of the ligated sequence-known cDNA fragment and the ligated sequence-unknown cDNA, a second primer which hybridizes with the known base sequence of the oligomer of the second single strand of the ligated sequence-known cDNA fragment and the ligated sequence-unknown cDNA, and a specific primer that hybridizes specifically with a base sequence of the first single strand of the ligated sequence-known cDNA fragment at a position between a base sequence complementary with the first primer and a base sequence complementary with the second primer,
   wherein, by using the first primer, the second primer, and the specific primer at the same time, and by competitive reactions occurring between PCR by the first primer and the second primer and PCR by the second primer and the specific primer, the double stranded fragments each having a part of the base sequence of the sequence-known DNA fragment and having a shorter length than the lengths of PCR products by the first and second primers are produced as major products in the PCR by the second primer and the specific primer.

12. A DNA preparation method according to claim 11, wherein the first primer or the second primer is labeled with a fluorophore and the specific primer is labeled with another fluorophore different from the fluorophore labeling the first primer or the second primer.

13. A DNA preparation method according to claim 11, wherein the first primer is labeled with a fluorophore and the specific primer is labeled with another fluorophore different from the fluorophore labeling the first primer.

14. A DNA preparation method according to claim 11, wherein the specific primer is only labeled with a fluorophore.

15. A DNA preparation method according to claim 11, wherein the first primer is only labeled with a fluorophore.

* * * * *